(12) United States Patent
Heusser et al.

(10) Patent No.: US 9,382,326 B2
(45) Date of Patent: Jul. 5, 2016

(54) COMPOSITIONS AND METHODS OF USE FOR THERAPEUTIC ANTIBODIES

(75) Inventors: Christoph Heusser, Oberwil (CH); Julia Neugebauer, Munich (DE); Eveline Schaadt, Munich (DE); Stefanie Urlinger, Munich (DE); Maximilian Woisetschlaeger, Perchtoldsdorf (AT)

(73) Assignee: Novartis AG, Basel (CH)

(*) Notice: Subject to any disclaimer, the term of this patent is extended or adjusted under 35 U.S.C. 154(b) by 931 days.

(21) Appl. No.: 13/326,569

(22) Filed: Dec. 15, 2011

(65) Prior Publication Data

US 2012/0195913 A1 Aug. 2, 2012

Related U.S. Application Data

(63) Continuation of application No. 12/503,175, filed on Jul. 15, 2009, now Pat. No. 8,106,163.

(30) Foreign Application Priority Data

Jul. 17, 2008 (EP) .................................. 08160671
May 15, 2009 (EP) .................................. 09160326

(51) Int. Cl.
*C07K 16/00* (2006.01)
*C07K 16/28* (2006.01)
*A61K 39/00* (2006.01)

(52) U.S. Cl.
CPC ........ *C07K 16/2878* (2013.01); *A61K 2039/505* (2013.01); *C07K 2317/21* (2013.01); *C07K 2317/34* (2013.01); *C07K 2317/55* (2013.01); *C07K 2317/56* (2013.01); *C07K 2317/565* (2013.01); *C07K 2317/73* (2013.01); *C07K 2317/74* (2013.01); *C07K 2317/76* (2013.01)

(58) Field of Classification Search
None
See application file for complete search history.

(56) References Cited

U.S. PATENT DOCUMENTS 7,083,785 B2    8/2006   Browning

FOREIGN PATENT DOCUMENTS

| WO | WO-0224909    | 3/2002 |
| WO | 2006/073941 A2 | 7/2006 |
| WO | 2008/008482 A2 | 1/2008 |

OTHER PUBLICATIONS

Eisenberg, Robert, "Combination biologics: 1 stone, 2 birds"; Blood 110(12):3817 (Dec. 2007).
Lee, Chingwei et al., "Synthetic anti-BR3 antibodies that mimic BAFF binding and target both human and murine B cells"; Blood 108(9):3103-3111 (Nov. 1, 2006).
Lin, Wei Yu et al.; "Anti-BR3 antibodies: a new class of B-cell immunotherapy combining cellular depletion and survival blockade"; Blood; 110(12):3959-3967 (Dec. 1, 2007).
Ng, Lai Guan et al.; "B Cell-Activating Factor Belonging to the TNF Family (BAFF)-R Is the Principal BAFF Receptor Facilitating BAFF Costimulation of Circulating T and B Cells"; J. Immunology; 173(2):807-817 (2004).
Zhang, Xin et al.; "BAFF supports human B cell differentiation in the lymphoid follicles through distinct receptors"; International Immunology; 17(6):779-788 (2005).
Rudikoff et al., "Single Amino Acid Substitution Altering Antigen-Binding Specificity," Proc. Natl. Acad. Sci. USA 79 (6):1979-1983 (Mar. 1982).
Colman, P.M., "Effects of Amino Acid Sequence Changes on ANtibody-Antigen Interactions," Research in Immunology 145:33-36 (1984).
MacCallum et al., "Antibody-Antigen Interactions: Contact Analysis and Binding Site Topography," J. Mol. Biol. 262:732-745 (1996).
Masuda et al., "The role of interface framework residues in determining antibody Vh/Vl interaction strength and antigen-binding affinity," FEBS Journal 273:2184-2194 (2006).
Paul, Fundamental Immunology, 3rd Edition. 1993, pp. 292-295.

*Primary Examiner* — Mark Halvorson

(57) ABSTRACT

The present invention relates to antibodies that specifically bind to the BAFF receptor (BAFFR). The invention more specifically relates to specific antibodies that are BAFFR antagonists with in vivo B cell depleting activity and compositions and methods of use for said antibodies to treat pathological disorders that can be treated by killing or depleting B cells, such as systemic lupus erythematosus or rheumatoid arthritis or other autoimmune diseases or lymphomas, leukemias and myelomas.

10 Claims, 4 Drawing Sheets

COMPOSITIONS AND METHODS OF USE FOR THERAPEUTIC ANTIBODIES

This application is a continuation of U.S. patent application Ser. No. 12/503,175, filed Jul. 15, 2009 which claims benefit under 35 U.S.C. §119(a)-(d) or (f) or 365(b) of EP Application No. 08160671.7, filed Jul. 17, 2008, and EP Application No. 09160326.6, filed May 15, 2009, the contents of which are incorporated herein by reference in their entirety.

The present invention relates to antibodies that specifically bind to the BAFF receptor (BAFFR). The invention more specifically relates to specific antibodies that are BAFFR antagonists with in vivo B cell depleting activity and compositions and methods of use for said antibodies to treat pathological disorders that can be treated by killing or depleting B cells, such as systemic lupus erythematosus or rheumatoid arthritis or other autoimmune diseases or lymphomas, leukemias and myelomas.

BAFFR (also known as BR3, TNFRSF13C, or CD268) is a member of the tumor necrosis factor receptor superfamily. It is expressed predominantly on B-lymphocytes and on a subset of T-cells. BAFFR specifically binds the tumor necrosis factor family member BLyS (also known as BAFF, CD257, TALL-1, THANK, TNFSF13B, ZTNF4) which can be expressed by a variety of different cell types, most notably myeloid cells. Functionally, the BLyS/BAFFR ligand-receptor pair is critically involved in the maturation of immature transitional B-cells and for survival, migration and activation of mature B-cells including isotype class switching. BLyS can act alone or in concert with B-cell receptor (BCR), interleukin-4, interleukin-21 or CD40 ligand. Due to the presence of BAFFR on some T-cells, BLyS can act as co-stimulatory factor for T-cell activation. BLyS can also bind to two additional receptors found on B-cells, TACI and BCMA.

Overexpression of BLyS or BAFFR in mice leads to B-cell hyperplasia and development of systemic auto-immunity with classical features of systemic lupus erythematosus (SLE). In addition, diseased (NZBxNZW)F1 and autoimmune MRL-lpr/lpr mice which represent animal models of SLE contain increased BLyS concentrations in the serum and BLyS levels correlate with disease progression. Increased levels of BLyS are also found in human patients suffering from SLE, rheumatoid arthritis, Sjögren's syndrome, Wegener's granulomatosis and B-cell malignancies. Furthermore, the disease phenotype in animal models of auto-immune diseases such as rheumatoid arthritis (e.g. collagen induced arthritis), SLE and multiple sclerosis (e.g. experimental autoimmune encephalomyelitis) can be partially reverted by BLyS blockade with soluble receptor fusion proteins. Similarly, treatment with BAFFR:Fc fusion protein inhibits chronic graft-versus-host disease (cGVHD) by blocking B-cell survival. Clinical efficacy data with a blocking anti-BLyS antibody in rheumatoid arthritis and SLE patients underscore the pathogenic role of BLyS in these auto-immune disorders.

BLyS induced signaling also appears to be involved in survival of malignant B-cells. Apoptosis of B-CLL cells can be rescued by addition of recombinant BLyS or APRIL. Conversely, apoptosis of B-CLL cells is augmented by adding soluble BAFFR fusion proteins or by anti-APRIL antibodies, indicating that BLyS and APRIL could serve as autocrine growth factors for malignant B-cells. BAFFR is expressed on a variety of diseased tissue including multiple myeloma and non-Hodgkin's lymphoma. Currently available treatments for these autoimmune diseases are immunosuppressants with severe side effects that do not cure the disease but aim at improving the signs and symptoms of the disease (disease-modifying drugs). Most of the immunosuppressants currently used in SLE and RA like corticosteroids, cyclophosphamide, methotrexate and azathioprin lead to a general anti-inflammatory effect that carries the risk of severe infections since it affects all effector arms of the immune system. Therefore, there is still a need for compositions and methods to treat SLE and/or RA and other related autoimmune diseases, such as agents that interfere with BAFFR signaling in which BLyS is suspected to contribute to disease.

Therefore, in one aspect, the invention provides an antibody or a functional protein comprising an antigen-binding portion of said antibody for a target in BAFFR polypeptide (SEQ ID NO:87), characterized in that the antibody or functional protein specifically binds to BAFFR polypeptide. In one embodiment, the antibody or functional protein is from a mammal, having an origin such as human or camelid, or is a humanized antibody. In a particular embodiment, the anti-BAFFR antibody is characterized as having antigen-binding region that is specific for the target protein BAFFR and binds to BAFFR or a fragment of BAFFR.

In one embodiment, the antibodies according to the invention are BAFFR antagonists with no or low agonistic activity. In certain embodiments, the antibody or functional fragment binds the target protein BAFFR and decreases or inhibits BLyS binding to BAFFR. In a related embodiment, the antibody or functional fragment inhibits BLyS induced human B cell proliferation, and/or IgG1 production.

In another embodiment, the antibodies according to the invention deplete B cell in vitro and in vivo. More preferably, the antibodies of the invention are BAFFR antagonists with no agonistic activity and deplete human B cell in vitro and in vivo.

The binding may be determined by one or more assays that can be used to measure an activity which is either antagonism or agonism by the antibody. Preferably, the assays measure at least one of the effects of the antibody on BAFFR that include: BLyS induced human B cell proliferation, IgG1 production and/or human B cell depleting activity.

In another embodiment, the invention provides antibodies that specifically bind to BLyS binding region of BAFFR. In a related embodiment, the invention provides antibodies that bind to a region of BAFFR between amino acids 17 and 43 of SEQ ID NO:87 and for example, it binds at least to PTPCV-PAECFDLLVRHCVACGLLR (SEQ ID NO 88).

According to another particular embodiment, the antibodies bind to BAFFR with a $K_D$ of 100 nM or less, 10 nM or less, 1 nM or less, inhibit BLyS induced human B cell proliferation with an $IC_{50}$ around 10 nM or less, 1 nM or less or 100 pM or less and deplete B cells in vitro with an $EC_{50}$ of 10 nM or less, 1 nM or less or 100 pM or less.

In another related embodiment, the antibodies reduce the percentage of B cells in blood and tissue in vivo up to 70%, preferably 80%, and more preferably 90% in a mouse model as compared to untreated control animals.

In some particular embodiments, the antibodies of the invention do not cross-react with a BAFFR related protein, and more particularly do not cross-react with human TACI or BCMA receptor.

In another related embodiment, the antibodies according to the invention are fully human or humanized IgG1 antibodies with antibody dependent cellular cytotoxicity (ADCC) activity and bind to a region of BAFFR comprised between amino acids 17 and 43 of SEQ ID NO:87, and for example, at least the following peptides PTPCVPAECFDLLVRHC-VACGLLR (SEQ ID NO 88) and deplete B cells in vitro with an $EC_{50}$ of 10 nM or less, 1 nM or less or 100 pM or less.

In another related embodiment, the antibodies according to the invention are human antibodies produced by recombinant expression in a cell line lacking fucosyltransferase, for example a mammalian cell line with deficient expression of the FUT8 gene encoding fucosyltransferase, thereby increasing ADCC activity as compared with wild type cells expressing the FUT8 gene.

The present invention relates to isolated antibodies, particularly human or humanized antibodies, that interfere with, decrease or inhibit BLyS binding to BAFFR and that depletes B cells in vitro and in vivo. In certain embodiments, the antibodies of the invention are derived from particular heavy and light chain sequences and/or comprise particular structural features such as CDR regions comprising particular amino acid sequences. The invention provides isolated antibodies, methods of making such antibodies, immunoconjugates and multivalent or multispecific molecules comprising such antibodies and pharmaceutical compositions containing the antibodies, immunoconjugates or bispecific molecules of the invention. The invention also relates to methods of using the antibodies to inhibit, e.g., antagonize, function of BAFFR in order to delay, prevent, prevent the onset of, or inhibit development of a disorder or condition associated with the presence of BLyS and/or BAFFR, for example, resulting in the treatment of a pathological disorder that is mediated by BAFFR or that can be treated by killing or depleting B cells; for example, an autoimmune disease such as systemic lupus erythematosus (SLE) or rheumatoid arthritis (RA) or B cell neoplasm such as lymphomas, leukemias or myelomas. Thus, such antibodies, antibody fragments or antigen-binding proteins may find use prophylactically, preventatively, or as part of a treatment method.

In order that the present invention may be more readily understood, certain terms are first defined. Additional definitions are set forth throughout the detailed description.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" or "signaling activity" refers to a biochemical causal relationship generally initiated by a protein-protein interaction such as binding of a growth factor to a receptor, resulting in transmission of a signal from one portion of a cell to another portion of a cell. In general, the transmission involves specific phosphorylation of one or more tyrosine, serine, or threonine residues on one or more proteins in the series of reactions causing signal transduction. Penultimate processes typically include nuclear events, resulting in a change in gene expression.

The term BAFFR or BAFF receptor refers to human BAFFR as defined in SEQ ID NO: 87. PCT Patent Publications WO200004032 and WO2006073941 refer to anti-BAFFR antibodies in general. WO2006073941 describes specific anti-BAFFR antibodies.

The term "antibody" as referred to herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen (e.g., a portion of BAFFR). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding region" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds BAFFR is substantially free of antibodies that specifically bind antigens other than BAFFR). An isolated antibody that specifically binds BAFFR may, however, have cross-reactivity to other antigens, such as BAFFR molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik, et al. (2000. J Mol Biol 296, 57-86).

The structures and locations of immunoglobulin variable domains, e.g., CDRs, may be defined using well known numbering schemes, e.g., the Kabat numbering scheme, the Chothia numbering scheme, a combination of Kabat and Chothia (AbM), etc. (see, e.g., Sequences of Proteins of Immunological Interest, U.S. Department of Health and Human Services (1991), eds. Kabat et al.; Al Lazikani et al. (1997) J. Mol. Bio. 273:927 948).

The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM, IgE, IgG such as IgG1 or IgG2) that is provided by the heavy chain constant region genes.

The phrases "an antibody recognizing an antigen" and "an antibody specific for an antigen" are used interchangeably herein with the term "an antibody which binds specifically to an antigen".

As used herein, an antibody that "specifically binds to BAFFR polypeptide" is intended to refer to an antibody that binds to human BAFFR polypeptide with a $K_D$ of 100 nM or less, 10 nM or less, 1 nM or less. An antibody that "cross-reacts with an antigen other than BAFFR" is intended to refer to an antibody that binds that antigen with a $K_D$ of $0.5 \times 10^{-8}$ M or less, $5 \times 10^{-9}$ M or less, or $2 \times 10^{-9}$ M or less. An antibody that "does not cross-react with a particular antigen" is intended to refer to an antibody that binds to that antigen, with a $K_D$ of $1.5 \times 10^{-8}$ M or greater, or a $K_D$ of $5\text{-}10 \times 10^{-8}$ M or $1 \times 10^{-7}$ M or greater. In certain embodiments, such antibodies that do not cross-react with the antigen exhibit essentially undetectable binding against these proteins in standard binding assays.

As used herein, the term "antagonist antibody" is intended to refer to an antibody that reduces, decreases and/or inhibits BAFFR induced signaling activity in the presence of BLyS in a human B cell assay such as human B cell proliferation assay or human B cell IgG1 production assay. Examples of human B cell proliferation assay and IgG1 production assay are described in more details in the examples below. In some embodiments, the antibodies reduce, decrease or inhibit BLyS induced activity as measured in a human B cell proliferation assay at an $IC_{50}$ of 10 nM or less, 1 nM or less, or 100 pM or less. In some embodiments, the antibodies inhibit BLyS induced activity as measured in a IgG1 production assay at an $IC_{50}$ of 10 nM or less, 1 nM or less, or 100 pM or less.

As used herein, an antibody with "no agonistic activity" is intended to refer to an antibody that does not significantly increase BAFFR mediated signaling activity in the absence of BLyS in a cell-based assay, such as human B cell proliferation assay. Such assays are described in more details in the examples below.

As used herein, an antibody that depletes B cells in vitro is intended to refer to an antibody that depletes B cells with an $EC_{50}$ of 10 nM or less, preferably with an $EC_{50}$ of 1 nM or less, more preferably with an $EC_{50}$ of 100 pM, or less, as measured in a human B cell depletion assay (ADCC). Such assays are described in more details in the examples below.

As used herein, an antibody that depletes B cells in vivo is intended to refer to an antibody that reduces in vivo the percentage of B cells up to 70%, preferably 80% and more preferably 90%, as measured by fluorescence activated cell sorting (FACS) of B cells. Such assays are described in more details in the examples below.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

As used herein, the term "Affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

As used herein, the term "Avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

As used herein, the term "ADCC" or "antibody dependent cellular cytotoxicity" activity refers to human B cell depleting activity. ADCC activity can be measured by the human B cell depleting assays described above.

In order to obtain a higher avidity probe, a dimeric conjugate (two molecules of an antibody protein coupled to a FACS marker) can be constructed, thus making low affinity interactions (such as with the germline antibody) more readily detected by FACS. In addition, another means to increase the avidity of antigen binding involves generating dimers, trimers or multimers of any of the constructs described herein of the anti-BAFFR antibodies. Such multimers may be generated through covalent binding between individual modules, for example, by imitating the natural C-to-N-terminus binding or by imitating antibody dimers that are held together through their constant regions. The bonds engineered into the Fc/Fc interface may be covalent or non-covalent. In addition, dimerizing or multimerizing partners other than Fc can be used in BAFFR hybrids to create such higher order structures. For example, it is possible to use multimerizing domains such as trimerizing domain described in Borean (WO2004039841) or pentamerizing domain described in published patent application WO98/18943.

As used herein, the term "selectivity" for an antibody refers to an antibody that binds to a certain target polypeptide but not to closely related polypeptides.

As used herein, the term "high affinity" for an antibody refers to an antibody having a $K_D$ of 1 nM or less for a target antigen. As used herein, the term "subject" includes any human or nonhuman animal.

The term "nonhuman animal" includes all vertebrates, e.g., mammals and non-mammals, such as nonhuman primates, sheep, dogs, cats, horses, cows, chickens, amphibians, reptiles, etc.

As used herein, the term, "optimized" means that a nucleotide sequence has been altered to encode an amino acid sequence using codons that are preferred in the production cell or organism, generally a eukaryotic cell, for example, a cell of *Pichia*, a cell of *Trichoderma*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in CHO mammalian cells; however optimized expression of these sequences in other eukaryotic cells is also envisioned herein. The amino acid sequences encoded by optimized nucleotide sequences are also referred to as optimized.

Various aspects of the invention are described in further detail in the following subsections.

Standard assays to evaluate the binding ability of the antibodies toward BAFFR of various species are known in the art, including for example, ELISAs, western blots and RIAs. Suitable assays are described in detail in the Examples. The binding kinetics (e.g., binding affinity) of the antibodies also can be assessed by standard assays known in the art, such as by Biacore analysis. Assays to evaluate the effects of the antibodies on functional properties of BAFFR (e.g., receptor binding, preventing or inducing human B cell proliferation or IgG production) are described in further detail in the Examples.

Accordingly, an antibody that "inhibits" one or more of these BAFFR functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (e.g., or when a control antibody of irrelevant specificity is present). An antibody that inhibits BAFFR activity effects such a statistically significant decrease by at least 10% of the measured parameter, by at least 50%, 80% or 90%, and in certain embodiments an antibody of the invention may inhibit greater than 95%, 98% or 99% of BAFFR functional activity.

The terms "cross-block", "cross-blocked" and "cross-blocking" are used interchangeably herein to mean the ability of an antibody or other binding agent to interfere with the binding of other antibodies or binding agents to BAFFR in a standard competitive binding assay.

The ability or extent to which an antibody or other binding agent is able to interfere with the binding of another antibody or binding molecule to BAFFR, and therefore whether it can be said to cross-block according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-blocking uses an ELISA-based approach. Further details on both methods are given in the Examples.

According to the invention, a cross-blocking antibody or other binding agent according to the invention binds to BAFFR in the described BIAcore cross-blocking assay such that the recorded binding of the combination (mixture) of the antibodies or binding agents is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%), and more specifically between 65% and 0.1% (e.g. 65% to 4%) of maximum theoretical binding (as defined above) of the two antibodies or binding agents in combination An antibody is defined as cross-blocking in the ELISA assay as described in the Examples, if the solution phase anti-BAFFR antibody is able to cause a reduction of between 60% and 100%, specifically between 70% and 100%, and more specifically between 80% and 100%, of the BAFFR detection signal (i.e. the amount of BAFFR bound by the coated antibody) as compared to the BAFFR detection signal obtained in the absence of the solution phase anti-BAFFR antibody (i.e. the positive control wells).

Recombinant Antibodies

Antibodies of the invention include the human recombinant antibodies, isolated and structurally characterized as described, in the Examples. The $V_H$ amino acid sequences of isolated antibodies of the invention are shown in SEQ ID NOs: 50-56. The $V_L$ amino acid sequences of isolated antibodies of the invention are shown in SEQ ID NOs: 43-49 respectively. Examples of preferred full length light chain amino acid sequences of antibodies of the invention are shown in SEQ ID NO:71-74. Examples of preferred full length heavy chain amino acid sequences of antibodies of the invention are shown in SEQ ID NO:75-78 respectively. Other examples of preferred full length heavy and light chain amino acid sequences of antibodies are those encoded by corresponding DNA sequences contained in plasmids pBW510 and pBW512 as deposited by Novartis Pharma AG, Forum 1, CH-4002 Basel, Switzerland, in DSMZ on Apr. 29, 2009 with accession number DSM22542 and DSM22543 respectively. Other antibodies of the invention include amino acids that have been mutated by amino acid deletion, insertion or substitution, yet have at least 60, 70, 80, 90 or 95 percent identity in the CDR regions with the CDR regions depicted in the sequences described above, including CDR regions encoded by corresponding DNA sequences of plasmids pBW510 and pBW512 as deposited as deposited by Novartis Pharma AG, Forum 1, CH-4002 Basel, Switzerland, in DSMZ on Apr. 29, 2009 with accession number DSM22542 and DSM22543 respectively. In some embodiments, it include mutant amino acid sequences wherein no more than 1, 2, 3, 4 or 5 amino acids have been mutated by amino acid deletion, insertion or substitution in the CDR regions when compared with the CDR regions depicted in the sequence described above.

Further, variable heavy chain parental nucleotide sequences are shown in SEQ ID NO 64. Variable light chain parental nucleotide sequences are shown in SEQ ID NO 57. Full length light chain nucleotide sequences optimized for expression in a mammalian cell are shown in SEQ ID NOs 83-86. Full length heavy chain nucleotide sequences optimized for expression in a mammalian cell are shown in SEQ ID NOs 79-82. Other antibodies of the invention include amino acids or nucleic acids that have been mutated, yet have at least 60, 70, 80, 90 or 95 percent identity to the sequences described above. In some embodiments, it include mutant amino acid sequences wherein no more than 1, 2, 3, 4 or 5 amino acids have been mutated by amino acid deletion, insertion or substitution in the variable regions when compared with the variable regions depicted in the sequence described above.

Since each of these antibodies binds the same epitope and are progenies from the same parental antibody, the $V_H$, $V_L$, full length light chain, and full length heavy chain sequences (nucleotide sequences and amino acid sequences) can be "mixed and matched" to create other anti-BAFFR binding molecules of the invention. BAFFR binding of such "mixed and matched" antibodies can be tested using the binding assays described above and in the Examples (e.g., ELISAs). When these chains are mixed and matched, a $V_H$ sequence from a particular $V_H/V_L$ pairing should be replaced with a structurally similar $V_H$ sequence. Likewise a full length heavy chain sequence from a particular full length heavy chain/full length light chain pairing should be replaced with a structurally similar full length heavy chain sequence. Likewise, a $V_L$ sequence from a particular $V_H/V_L$ pairing should be replaced with a structurally similar $V_L$ sequence. Likewise a full length light chain sequence from a particular full length heavy chain/full length light chain pairing should be replaced with a structurally similar full length light chain sequence. Accordingly, in one aspect, the invention provides an isolated recombinant antibody or antigen binding region thereof having: a heavy chain variable region comprising an amino acid sequence selected from the group consisting of SEQ ID NOs: 50-56; and a light chain variable region comprising an amino acid sequence selected from the group consisting of SEQ ID NOs: 43-49; wherein the antibody specifically binds to BAFFR.

In another aspect, the invention provides
(i) an isolated recombinant antibody having: a full length heavy chain comprising an amino acid sequence selected from the group consisting of SEQ ID NOs:75-78; and a full length light chain comprising an amino acid sequence selected from the group consisting of SEQ ID NOs:71-74; wherein the antibody specifically binds to BAFFR, or
(ii) a functional protein comprising an antigen binding portion thereof.

In another aspect, the invention provides
(i) an isolated recombinant antibody having: a full length heavy chain encoded by a nucleotide sequence that has been optimized for expression in the cell of a mammalian selected from the group consisting of SEQ ID NOs: 79-82; and a full length light chain encoded by a nucleotide sequence that has been optimized for expression in the cell of a mammalian selected from the group consisting of SEQ ID NOs:83-86; wherein the antibody specifically binds to BAFFR; or,
(ii) a functional protein comprising an antigen binding portion thereof.

The amino acid sequences of the $V_H$ CDR1s of the antibodies are shown in SEQ ID NOs: 1-7. The amino acid sequences of the $V_H$ CDR2s of the antibodies are shown in SEQ ID NOs: 8-14. The amino acid sequences of the $V_H$ CDR3s of the antibodies are shown in SEQ ID NOs: 15-21. The amino acid sequences of the $V_L$ CDR1s of the antibodies are shown in SEQ ID NOs: 22-28. The amino acid sequences of the $V_L$ CDR2s of the antibodies are shown in SEQ ID NOs: 29-35. The amino acid sequences of the $V_L$ CDR3s of the antibodies are shown in SEQ ID NOs: 36-42. The CDR regions set forth in SEQ ID NOs:1-42 are delineated using the Kabat system (Kabat, E. A., et al., 1991 Sequences of Proteins of Immunological Interest, Fifth Edition, U.S. Department of Health and Human Services, NIH Publication No. 91-3242).

Given that each of these antibodies can bind to BAFFR and that antigen-binding specificity is provided primarily by the CDR1, 2 and 3 regions, the $V_H$ CDR1, 2 and 3 sequences and $V_L$ CDR1, 2 and 3 sequences can be "mixed and matched" (i.e., CDRs from different antibodies can be mixed and match, each antibody containing a $V_H$ CDR1, 2 and 3 and a $V_L$ CDR1, 2 and 3 create other anti-BAFFR binding molecules of the invention. BAFFR binding of such "mixed and matched" antibodies can be tested using the binding assays described above and in the Examples (e.g., ELISAs). When $V_H$ CDR sequences are mixed and matched, the CDR1, CDR2 and/or CDR3 sequence from a particular $V_H$ sequence should be replaced with a structurally similar CDR sequence(s). Likewise, when $V_L$ CDR sequences are mixed and matched, the CDR1, CDR2 and/or CDR3 sequence from a particular $V_L$ sequence should be replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences shown herein for monoclonal antibodies of the present invention.

In some embodiments, isolated recombinant antibodies, or antigen binding regions thereof have: a heavy chain variable region CDR1 comprising an amino acid sequence selected from the group consisting of SEQ ID NOs: 1-7; a heavy chain variable region CDR2 comprising an amino acid sequence selected from the group consisting of SEQ ID NOs: 8-14; a heavy chain variable region CDR3 comprising an amino acid sequence selected from the group consisting of SEQ ID NOs: 15-21; a light chain variable region CDR1 comprising an amino acid sequence selected from the group consisting of SEQ ID NOs: 22-28; a light chain variable region CDR2 comprising an amino acid sequence selected from the group consisting of SEQ ID NOs: 29-35; and a light chain variable region CDR3 comprising an amino acid sequence selected from the group consisting of SEQ ID NOs: 36-42; wherein the antibody specifically binds BAFFR.

In a certain embodiment, the antibody comprises: a heavy chain variable region CDR1 of SEQ ID NO: 2; a heavy chain variable region CDR2 of SEQ ID NO: 9; a heavy chain variable region CDR3 of SEQ ID NO: 16; a light chain variable region CDR1 of SEQ ID NO: 23; a light chain variable region CDR2 of SEQ ID NO: 30; and a light chain variable region CDR3 of SEQ ID NO: 37.

In a certain embodiment, the antibody comprises: a heavy chain variable region CDR1 of SEQ ID NO: 3; a heavy chain variable region CDR2 of SEQ ID NO: 10; a heavy chain variable region CDR3 of SEQ ID NO: 17; a light chain variable region CDR1 of SEQ ID NO: 24; a light chain variable region CDR2 of SEQ ID NO: 31; and a light chain variable region CDR3 of SEQ ID NO: 38.

In a certain embodiment, the antibody comprises: a heavy chain variable region CDR1 of SEQ ID NO: 4; a heavy chain variable region CDR2 of SEQ ID NO: 11; a heavy chain variable region CDR3 of SEQ ID NO: 18; a light chain variable region CDR1 of SEQ ID NO: 25; a light chain variable region CDR2 of SEQ ID NO: 32; and a light chain variable region CDR3 of SEQ ID NO: 39.

In a certain embodiment, the antibody comprises: a heavy chain variable region CDR1 of SEQ ID NO: 5; a heavy chain variable region CDR2 of SEQ ID NO: 12; a heavy chain variable region CDR3 of SEQ ID NO: 19; a light chain variable region CDR1 of SEQ ID NO: 26; a light chain variable region CDR2 of SEQ ID NO: 33; and a light chain variable region CDR3 of SEQ ID NO: 40.

In a certain embodiment, the antibody comprises: a heavy chain variable region CDR1 of SEQ ID NO: 6; a heavy chain variable region CDR2 of SEQ ID NO: 13; a heavy chain variable region CDR3 of SEQ ID NO: 20; a light chain variable region CDR1 of SEQ ID NO: 27; a light chain variable region CDR2 of SEQ ID NO: 34; and a light chain variable region CDR3 of SEQ ID NO: 41.

In a certain embodiment, the antibody comprises: a heavy chain variable region CDR1 of SEQ ID NO: 7; a heavy chain variable region CDR2 of SEQ ID NO: 14; a heavy chain variable region CDR3 of SEQ ID NO: 21; a light chain variable region CDR1 of SEQ ID NO: 28; a light chain variable region CDR2 of SEQ ID NO: 35; and a light chain variable region CDR3 of SEQ ID NO: 42.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention has full length heavy and light chain amino acid sequences; full length heavy and light chain nucleotide sequences, variable region heavy and light chain nucleotide sequences, or variable region heavy and light chain amino acid sequences that are homologous to the amino acid and nucleotide sequences of the antibodies described herein, and wherein the antibodies retain the desired functional properties of the anti-BAFFR antibodies of the invention.

For example, the invention provides an isolated recombinant antibody (or a functional protein comprising an antigen binding portion thereof) comprising a heavy chain variable region and a light chain variable region, wherein: the heavy chain variable region comprises an amino acid sequence that is at least 80%, or at least 90% identical to an amino acid sequence selected from the group consisting of SEQ ID NOs: 50-56; the light chain variable region comprises an amino acid sequence that is at least 80%, or at least 90% identical to an amino acid sequence selected from the group consisting of SEQ ID NOs: 43-49; the antibody specifically binds to BAFFR, and the antibody exhibits at least one of the following functional properties: it inhibits BLyS induced B cell proliferation, or BLyS induced IgG1 production and it depletes B cell in vitro or in vivo.

In a further example, the invention provides an isolated recombinant antibody, (or a functional protein comprising an antigen binding portion thereof) comprising a full length heavy chain and a full length light chain, wherein: the full length heavy chain comprises an amino acid sequence that is at least 80%, or at least 90% identical to an amino acid sequence selected from the group consisting of SEQ ID NOs 75-78; the full length light chain comprises an amino acid sequence that is at least 80%, or at least 90% identical to an amino acid sequence selected from the group consisting of SEQ ID NOs 71-74; the antibody specifically binds to BAFFR, and the antibody exhibits at least one of the following functional properties: it inhibits BLyS induced B cell proliferation, or BLyS induced IgG1 production and it depletes B cell in vitro or in vivo.

In another example, the invention provides an isolated recombinant antibody (or a functional protein comprising an antigen binding portion thereof), comprising a full length heavy chain and a full length light chain, wherein: the full length heavy chain is encoded by a nucleotide sequence that is at least 80%, or at least 90% identical to a nucleotide sequence selected from the group consisting of SEQ ID NOs 79-82; the full length light chain is encoded by a nucleotide sequence that is at least 80%, or at least 90% identical to a nucleotide sequence selected from the group consisting of SEQ ID NOs 83-86; the antibody specifically binds to BAFFR, and the antibody exhibits at least one of the following functional properties: it inhibits BLyS induced B cell proliferation, or BLyS induced IgG1 production and it depletes B cell in vitro or in vivo.

In various embodiments, the antibody may exhibit one or more, two or more, or three of the functional properties discussed above. The antibody can be, for example, a human antibody, a humanized antibody or a chimeric antibody. Preferably the antibody is a fully human IgG1 antibody.

In other embodiments, the $V_H$ and/or $V_L$ amino acid sequences may be 50%, 60%, 70%, 80%, 90%, 95%, 96%, 97%, 98% or 99% identical to the sequences set forth above.

In other embodiments, the $V_H$ and/or $V_L$ amino acid sequences may be identical except an amino acid substitution in no more than 1, 2, 3, 4 or 5 amino acid position. An antibody having $V_H$ and $V_L$ regions having high (i.e., 80% or greater) identity to the $V_H$ and $V_L$ regions of SEQ ID NOs 50-56 and SEQ ID NOs 43-49 respectively, can be obtained by mutagenesis (e.g., site-directed or PCR-mediated mutagenesis) of nucleic acid molecules encoding SEQ ID NOs: 64-70 and 57-63 respectively, followed by testing of the encoded altered antibody for retained function (i.e., the functions set forth above) using the functional assays described herein.

In other embodiments, the full length heavy chain and/or full length light chain amino acid sequences may be 50% 60%, 70%, 80%, 90%, 95%, 96%, 97%, 98% or 99% identical to the sequences set forth above. An antibody having a full length heavy chain and full length light chain having high (i.e., 80% or greater) identity to the full length heavy chains of any of SEQ ID NOs 75-78 and full length light chains of any of SEQ ID NOs 71-74 respectively, can be obtained by mutagenesis (e.g., site-directed or PCR-mediated mutagenesis) of nucleic acid molecules encoding SEQ ID NOs 79-82 and SEQ ID NOs 83-86 respectively, followed by testing of the encoded altered antibody for retained function (i.e., the functions set forth above) using the functional assays described herein.

In other embodiments, the full length heavy chain and/or full length light chain nucleotide sequences may be 60%, 70%, 80%, 90%, 95%, 96%, 97%, 98% or 99% identical to the sequences set forth above.

In other embodiments, the variable regions of heavy chain and/or light chain nucleotide sequences may be 60%, 70%, 80%, 90%, 95%, 96%, 97%, 98% or 99% identical to the sequences set forth above As used herein, the percent identity between the two sequences is a function of the number of identical positions shared by the sequences (i.e., % identity=# of identical positions/total # of positions ×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the anti-BAFFR antibodies of the invention. Accordingly, the invention provides an isolated recombinant antibody, or a functional protein comprising an antigen binding portion thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs:1-7, and conservative modifications thereof; the heavy chain variable region CDR2 amino acid sequences are selected from the group consisting of SEQ ID NOs: 8-14, and conservative modifications thereof; the heavy chain variable region CDR3 amino acid sequences are selected from the group consisting of SEQ ID NOs: 15-21, and conservative modifications thereof; the light chain variable regions CDR1 amino acid sequences are selected from the group consisting of SEQ ID NOs: 22-28, and conservative modifications thereof; the light chain variable regions CDR2 amino acid sequences are selected from the group consisting of SEQ ID NOs: 29-35, and conservative modifications thereof; the light chain variable regions of CDR3 amino acid sequences are selected from the group consisting of SEQ ID NOs: 36-42, and conservative modifications thereof; the antibody specifically binds to BAFFR, and the antibody exhibits at least one of the following functional properties: it inhibits BLyS induced B cell proliferation, or BLyS induced IgG1 production and it depletes B cells in vitro or in vivo.

In various embodiments, the antibody may exhibit one or more, two or more, or three or more of the functional properties listed discussed above. Such antibodies can be, for example, human antibodies, humanized antibodies or chimeric antibodies.

In other embodiments, an antibody of the invention optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the anti-BAFFR antibodies of the invention. Accordingly, the invention provides an isolated monoclonal antibody optimized for expression in a mammalian cell consisting of a full length heavy chain and a full length light chain wherein: the full length heavy chain has amino acid sequences selected from the group of SEQ ID NOs: 75-78, and conservative modifications thereof; and the full length light chain has amino acid sequences selected from the group of SEQ ID NOs: 71-74, and conservative modifications thereof; the antibody specifically binds to BAFFR; and the antibody exhibits at least one of the following functional properties: it inhibits BLyS induced B cell proliferation, or BLyS induced IgG1 production and it depletes B cell in vitro or in vivo.

In various embodiments, the antibody may exhibit one or more, two or more, or three or more of the functional properties listed discussed above. Such antibodies can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

Antibodies that Bind to the Same Epitope as Anti-Baffr Antibodies of the Invention In another embodiment, the invention provides antibodies that bind to the same epitope as do the various specific anti-BAFFR antibodies of the invention described herein. All the antibodies described in the Examples that are capable of blocking the BLyS induced effect bind the same epitope in BAFFR with high affinity, said epitope being comprised between amino acids of SEQ ID NO:88.

Additional antibodies can therefore be identified based on their ability to cross-compete (e.g., to competitively inhibit the binding of, in a statistically significant manner) with other antibodies of the invention in standard BAFFR binding assays. The ability of a test antibody to inhibit the binding of antibodies of the present invention to human BAFFR demonstrates that the test antibody can compete with that antibody for binding to human BAFFR; such an antibody may, according to non-limiting theory, bind to the same or a related (e.g., a structurally similar or spatially proximal) epitope on human BAFFR as the antibody with which it competes. Thus, another aspect of the invention provides antibodies that bind to the same antigen as, and compete with, the antibodies disclosed herein by sequence. In a certain embodiment, the antibody that binds to the same epitope on human BAFFR as the antibodies of the present invention is a human recombinant antibody. Such human recombinant antibodies can be prepared and isolated as described in the Examples.

Engineered and Modified Antibodies

An antibody of the invention further can be prepared using an antibody having one or more of the $V_H$ and/or $V_L$ sequences shown herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad. See. U.S.A. 86:10029-10033; U.S. Pat. No. 5,225,539 to winter, and U.S. Pat. Nos. 5,530,101; 5,585,089; 5,693,762 and 6,180,370 to Queen et al.)

Accordingly, another embodiment of the invention pertains to an isolated monoclonal anti-BAFFR antibody, or a functional protein comprising an antigen binding portion thereof, comprising a heavy chain variable region comprising CDR1 sequences having an amino acid sequence selected from the group consisting of SEQ ID NOs: 1-7; CDR2 sequences having an amino acid sequence selected from the group consisting of SEQ ID NOs: 8-14; CDR3 sequences having an amino acid sequence selected from the group consisting of SEQ ID NOs: 15-21, respectively; and a light chain variable region having CDR1 sequences having an amino acid sequence selected from the group consisting of SEQ ID NOs: 22-28; CDR2 sequences having an amino acid sequence selected from the group consisting of SEQ ID NOs: 29-35; and CDR3 sequences consisting of an amino acid sequence selected from the group consisting of SEQ ID NOs: 36-42, respectively. Thus, such antibodies contain the $V_H$ and $V_L$ CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J. Immunol. 24:827-836.

An example of framework sequences for use in the antibodies of the invention are those that are structurally similar to the framework sequences used by selected antibodies of the invention, e.g., consensus sequences and/or framework sequences used by monoclonal antibodies of the invention. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the invention provides isolated anti-BAFFR monoclonal antibodies, or a functional protein comprising an antigen binding portion thereof, consisting of a heavy chain variable region having: a $V_H$ CDR1 region consisting of an amino acid sequence selected from the group having SEQ ID NOs: 1-7 or an amino acid sequence having one, two, three, four or five amino acid substitutions, deletions or additions as compared to SEQ ID NOs: 1-7; a $V_H$ CDR2 region having an amino acid sequence selected from the group consisting of SEQ ID NOs: 8-14, or an amino acid sequence having one, two, three, four or five amino acid substitutions, deletions or additions as compared to SEQ ID NOs: 8-14; a $V_H$ CDR3 region having an amino acid sequence selected from the group consisting of SEQ ID NOs: 15-21, or an amino acid sequence having one, two, three, four or five amino acid substitutions, deletions or additions as compared to SEQ ID NOs: 15-21; a $V_L$ CDR1 region having an amino acid sequence selected from the group consisting of SEQ ID NOs: 22-28, or an amino acid sequence having one, two, three, four or five amino acid substitutions, deletions or additions as compared to SEQ ID NOs: 22-28; a $V_L$ CDR2 region having an amino acid sequence selected from the group consisting of SEQ ID NOs: 29-35, or an amino acid sequence having one, two, three, four or five amino acid substitutions, deletions or additions as compared to SEQ ID NOs: 29-35; and a $V_L$ CDR3 region having an amino acid sequence selected from the group consisting of SEQ ID NOs: 36-42, or an amino acid sequence having one, two, three, four or five amino acid substitutions, deletions or additions as compared to SEQ ID NOs: 36-42.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to BAFFR. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target protein of SEQ ID NO: 87. Such compounds are known herein as "polypeptides comprising a target-specific binding region". Examples of non-immunoglobulin framework are further described in the sections below (camelid antibodies and non-antibody scaffold).

Camelid Antibodies

Antibody proteins obtained from members of the camel and dromedary (Camelus bactrianus and Calelus dromaderius) family including new world members such as llama species (Lama paccos, Lama glama and Lama vicugna) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as $V_{HH}$ can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J. 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as E. coli and are expressed as fusion proteins with bacteriophage and are functional.

Accordingly, a feature of the present invention is a camelid antibody or nanobody having high affinity for BAFFR. In certain embodiments herein, the camelid antibody or nanobody is naturally produced in the camelid animal, i.e., is produced by the camelid following immunization with BAFFR or a peptide fragment thereof, using techniques described herein for other antibodies. Alternatively, the anti-BAFFR camelid nanobody is engineered, i.e., produced by selection for example from a library of phage displaying appropriately mutagenized camelid nanobody proteins using panning procedures with BAFFR as a target as described in the examples herein. In one embodiement, an antibody of the disclosure is camelized, having a camelid framework and $V_H$ CDR1, CDR2 and/or CDR3 regions as disclosed herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Non-Antibody Scaffold

Known non-immunoglobulin frameworks or scaffolds include, but are not limited to, Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immunopharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany), protein epitope mimetics (Polyphor Ltd, Allschwil, Switzerland).

(i) Fibronectin Scaffold

The fibronectin scaffolds are based preferably on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

(ii) Ankyrin—Molecular Partners

The technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

(iii) Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, 20040175756; 20050053973; 20050048512; and 20060008844.

(vi) Protein A—Affibody

Affibody® affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g., U.S. Pat. No. 5,831,012). Affibody® molecules mimic antibodies, they have a molecular weight of 6 kDa, compared to the molecular weight of antibodies, which is 150 kDa. In spite of its small size, the binding site of Affibody® molecules is similar to that of an antibody.

(v) Anticalins—*Pieris*

Anticalins® are products developed by the company *Pieris ProteoLab AG*. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target molecules of different shape with high affinity and specificity.

One protein of lipocalin family, the bilin-binding protein (BBP) of *Pieris Brassicae* has been used to develop anticalins by mutagenizing the set of four loops. One example of a patent application describing "anticalins" is PCT WO 199916873.

(vi) Affilin—Scil Proteins

Affilin™ molecules are small non-immunoglobulin proteins which are designed for specific affinities towards proteins and small molecules. New Affilin™ molecules can be very quickly selected from two libraries, each of which is based on a different human derived scaffold protein.

Affilin™ molecules do not show any structural homology to immunoglobulin proteins. Scil Proteins employs two Affilin™ scaffolds, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368

(vii) Protein Epitope Mimetics (PEM)

PEM are medium-sized, cyclic, peptide-like molecules (MW 1-2 kDa) mimicking beta-hairpin secondary structures of proteins, the major secondary structure involved in protein-protein interactions.

Framework or Fc Engineering

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et at.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in one embodiment, the antibodies of the invention are produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lecl3 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Eureka Therapeutics further describes genetically engineered CHO mammalian cells capable of producing antibodies with altered mammalian glycosylation pattern devoid of fucosyl residues. Alternatively, the antibodies of the invention can be produced in yeasts or filamentous fungi engineered for mammalian-like glycosylation pattern and capable of producing antibodies lacking fucose as glycosylation pattern (see for example EP1297172B1).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP0322094.

Another possibility is a fusion of at least the antigen-binding region of the antibody of the invention to proteins capable of binding to serum proteins, such human serum albumin to increase half life of the resulting molecule. Such approach is for example described in Nygren et al., EP 0 486 525.

Methods of Engineering Altered Antibodies

As discussed above, the anti-BAFFR antibodies having $V_H$ and $V_L$ sequences or full length heavy and light chain sequences shown herein can be used to create new anti-BAFFR antibodies by modifying full length heavy chain and/or light chain sequences, $V_H$ and/or $V_L$ sequences, or the constant region(s) attached thereto. Thus, in another aspect of the invention, the structural features of an anti-BAFFR antibody of the invention are used to create structurally related anti-BAFFR antibodies that retain at least one functional property of the antibodies of the invention, such as binding to human BAFFR and also inhibiting one or more functional properties of BAFFR (e.g., antagonistic activity, B cell depleting activity).

For example, one or more CDR regions of the antibodies of the present invention, or mutations thereof, can be combined recombinantly with known framework regions and/or other CDRs to create additional, recombinantly-engineered, anti-BAFFR antibodies of the invention, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-BAFFR antibody consisting of: a heavy chain variable region antibody sequence having a CDR1 sequence selected from the group consisting of SEQ ID NOs: 1-7, a CDR2 sequence selected from the group consisting of SEQ ID NOs: 8-14 and/or a CDR3 sequence selected from the group consisting of SEQ ID NOs: 15-21; and a light chain variable region antibody sequence having a CDR1 sequence selected from the group consisting of SEQ ID NOs: 22-28, a CDR2 sequence selected from the group consisting of SEQ ID NOs: 29-35 and/or a CDR3 sequence selected from the group consisting of SEQ ID NOs: 36-42; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing an anti-BAFFR antibody optimized for expression in a mammalian cell consisting of: a full length heavy chain antibody sequence having a sequence selected from the group of SEQ ID NOs: 75-78; and a full length light chain antibody sequence having a sequence selected from the group of 71-74; altering at least one amino acid residue within the full length heavy chain antibody sequence and/or the full length light chain antibody sequence to create at least one altered antibody sequence; and expressing the altered antibody sequence as a protein.

The altered antibody sequence can also be prepared by screening antibody libraries having fixed CDR3 sequences selected among the group consisting of SEQ ID NO:15-21 and SEQ ID NO: 36-42 or minimal essential binding determinants as described in US20050255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the anti-BAFFR antibodies described herein, which functional properties include, but are not limited to, specifically binding to human BAFFR; and/or it inhibits BLyS induced B cell proliferation, BLyS induced B or BLyS induced IgG1 production; and/or depletes human B cell in vitro or in vivo.

The altered antibody may exhibit one or more, two or more, or three or more of the functional properties discussed above.

The functional properties of the altered antibodies can be assessed using standard assays available in the art and/or described herein, such as those set forth in the Examples (e.g., ELISAs).

In certain embodiments of the methods of engineering antibodies of the invention, mutations can be introduced randomly or selectively along all or part of an anti-BAFFR antibody coding sequence and the resulting modified anti-BAFFR antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. Examples of full length light chain nucleotide sequences optimized for expression in a mammalian cell are shown in SEQ ID NOs:83-86. Examples of full length heavy chain nucleotide sequences optimized for expression in a mammalian cell are shown in SEQ ID NOs: 79-82.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from various phage clones that are members of the library. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. In some embodiments, the heavy chain constant region is selected among IgG1 isotypes. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, $C_L$. The sequences of human light chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ regions joined by the flexible linker (see e.g., Bird et al., 1988 Science 242:423-426; Huston et at., 1988 Proc. Natl. Acad. Sci. USA 85:5879-5883; McCafferty et al., 1990 Nature 348:552-554).

Generation of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain embodiment, the antibodies of the invention are human monoclonal antibodies. Such human monoclonal antibodies directed against BAFFR can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N.Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et at., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851). See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-BAFFR antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114, 598; 6, 150,584 and 6,162,963 to Kucherlapati et al.

Moreover, alternative transchromosomic animal systems expressing human immunoglobulin genes are available in the art and can be used to raise anti-BAFFR antibodies of the invention. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise anti-BAFFR antibodies of the invention.

Human recombinant antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Generation of Hybridomas Producing Human Monoclonal Antibodies

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3×63-Ag8.653 nonsecreting mouse myeloma cells (ATCC, CRL 1580) with 50% PEG. Cells are plated at approximately 2×145 in flat bottom microtiter plates, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0:055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13).

Mammalian host cells for expressing the recombinant antibodies of the invention include Chinese Hamster Ovary (CHO cells) (including dhfr-CHO cells, described Urlaub and Chasin, 1980 Proc. Natl. Acad. Sci. USA 77:4216-4220 used with a DH FR selectable marker, e.g., as described in R. J. Kaufman and P. A. Sharp, 1982 Mol. Biol. 159:601-621, NSO myeloma cells, COS cells and SP2 cells). In particular, for use with NSO myeloma cells, another expression system is the GS gene expression system shown in WO 87/04462, WO 89/01036 and EP 338,841. In one embodiment, mammalian host cells for expressing the recombinant antibodies of the invention include mammalian cell lines deficient for FUT8 gene expression, for example as described in U.S. Pat. No. 6,946,292B2. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

Immunoconjugates

In another aspect, the present invention features an anti-BAFFR antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al., 2003 Adv. Drug Deliv. Rev. 55:199-215; Trail, P. A. et al., 2003 Cancer Immunol. Immunother. 52:328-337; Payne, G., 2003 Cancer Cell 3:207-212; Allen, T. M., 2002 Nat. Rev. Cancer 2:750-763; Pastan, I. and Kreitman, R. J., 2002 Curr. Opin. Investig. Drugs 3:1089-1091; Senter, P. D. and Springer, C. J., 2001 Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Method for preparing radioimmunconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et at., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific or multispecific molecules comprising an anti-BAFFR antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for BAFFR and a second binding specificity for a second target epitope. For example, the second target epitope is another epitope of BAFFR different from the first target epitope. Another example is a bispecific molecule comprising at least one first binding specificity for BAFFR and a second binding specificity for an epitope within CD20.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

Other antibodies which can be employed in the bispecific molecules of the invention are murine, chimeric and humanized monoclonal antibodies.

The bispecific molecules of the present invention can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccininnidyl 4-(N-maleimidomethyl)cyclohaxane-1-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat.

No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

Multivalent Antibodies

In another aspect, the present invention provides multivalent antibodies comprising at least two identical or different antigen-binding portions of the antibodies of the invention binding to BAFFR. In one embodiment, the multivalent antibodies provides at least two, three or four antigen-binding portions of the antibodies. The antigen-binding portions can be linked together via protein fusion or covalent or non covalent linkage. Alternatively, methods of linkage have been described for the bispecific molecules. Tetravalent compounds can be obtained for example by cross-linking antibodies of the antibodies of the invention with an antibody that binds to the constant regions of the antibodies of the invention, for example the Fc or hinge region.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies that bind to different epitopes on the target antigen or that have complementary activities.

Pharmaceutical compositions of the invention also can be administered in combination therapy, i.e., combined with other agents. For example, the combination therapy can include an anti-BAFFR antibody of the present invention combined with at least one other anti-inflammatory or another chemotherapeutic agent, for example, a cytotoxic, anti-cancer or anti-proliferative agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al., 1977 J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Reviews on the development of stable protein (e.g., antibody) formulations may be found in Cleland et al. (1993) Crit. Reviews. Ther. Drug Carrier Systems 10(4):307-377 and Wei Wang (1999) Int. J. Pharmaceutics 185:129-88. Additional formulation discussions for antibodies may be found, e.g., in Daugherty and Mrsny (2006) Advanced Drug Delivery Reviews 58: 686-706; U.S. Pat. No. 6,171,586; U.S. Pat. No. 4,618,486; US20060286103; WO06044908; WO07095337; WO04016286; Colandene et al. (2007) J. Pharm. Sci 96:1598-1608; Schulman (2001) Am. J. Respir. Crit. Care Med. 164:S6-S11 and other known references.

Solutions or suspensions used for intradermal or subcutaneous application typically include one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic.

Sterile injectable solutions can be prepared by incorporating the antibody of the invention in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

When a therapeutically effective amount of an antibody of the invention is administered by, e.g., intravenous, cutaneous or subcutaneous injection, the binding agent will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to binding agents, an isotonic vehicle such as sodium chloride injection, Ringer's injection, dextrose injection, dextrose and sodium chloride injection, lactated Ringer's injection, or other vehicle as known in the art. The pharmaceutical connposition(s) of the present disclosure may also contain stabilizers, preservatives, buffers, antioxidants, or other additive known to those of skill in the art.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Dosage regimens for an anti-BAFFR antibody of the invention include 1 mg/kg body weight or 3 mg/kg body weight by intravenous administration, with the antibody being given using one of the following dosing schedules: every four weeks for six dosages, then every three months; every three weeks; 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-BAFFR antibody of the invention can results in a decrease in severity of disease symptoms, an increase in frequency and duration of disease symptom-free periods, or a prevention of impairment or disability due to the disease affliction.

A composition of the present invention can be administered by one or more routes of administration using one or more of a variety of methods known in the art. As will be appreciated by the skilled artisan, the route and/or mode of administration will vary depending upon the desired results. Routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastennal injection and infusion.

Alternatively, an antibody of the invention can be administered by a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in one embodiment, a therapeutic composition of the invention can be administered with a needleless hypodermic injection device, such as the devices shown in U.S. Pat. Nos. 5,399,163; 5,383, 851; 5,312,335; 5,064,413; 4,941,880; 4,790,824 or 4,596, 556. Examples of well known implants and modules useful in the present invention include: U.S. Pat. No. 4,487,603, which shows an implantable micro-infusion pump for dispensing medication at a controlled rate; U.S. Pat. No. 4,486,194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989 J. Cline Pharmacol. 29:685). Exemplary targeting moieties include folate or biotin (see, e.g., U.S. Pat. No. 5,416,016 to Low et al.); mannosides (Umezawa et al., 1988 Biochem. Biophys. Res. Commun. 153:1038); antibodies (P. G. Bloeman et al., 1995 FEBS Lett. 357:140; M. Owais et al., 1995 Antimicrob. Agents Chemother. 39:180); surfactant protein A receptor (Briscoe et al., 1995 Am. J. Physiol. 1233:134); p 120 (Schreier et al., 1994 J. Biol. Chem. 269:9090); see also K. Keinanen; M. L. Laukkanen, 1994 FEBS Lett. 346:123; J. J. Killion; I. J. Fidler, 1994 Immunomethods 4:273.

Uses and Methods of the Invention

The antibodies of the present invention have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders. The term "subject" as used herein is intended to include human and non-human animals. Non-human animals include all vertebrates, e.g., mammals and non-mammals, such as non-human primates, sheep, dogs, cats, cows, horses, chickens, amphibians, and reptiles.

The methods are particularly suitable for treating, preventing or diagnosing BAFFR-related disorders and/or autoimmune diseases, e.g., systemic lupus erythematosus or rheumatoid arthritis.

The invention also provides methods for depleting B cells in an animal, preferably depleting or killing human B cell by administering a composition comprising a therapeutically efficient dose of the antibodies of the invention.

As used herein, "a BAFFR-related disorder" includes conditions associated with or characterized by aberrant BLyS levels and/or diseases or conditions that can be treated by depleting or killing B cells. These include inflammatory conditions, allergies and allergic conditions, hypersensitivity reactions, autoimmune diseases, severe infections, and organ or tissue transplant rejection. These further include B-cell neoplasms.

For example, the antibodies of the invention may be used for the treatment of recipients of heart, lung, combined heart-lung, liver, kidney, pancreatic, skin or corneal transplants, including allograft rejection or xenograft rejection, and for the prevention of graft-versus-host disease, such as following bone marrow transplant, and organ transplant associated arteriosclerosis.

The antibodies of the invention are useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankolsing spondylitis, Reiter syndrome, reactive arthritis, psoriatic arthritis, and enterophathics arthritis, hypersensitivity (including both airways hypersensitivity and dermal hypersensitivity) and allergies. Specific auto-immune diseases for which antibodies of the invention may be employed include autoimmune haematological disorders (including e.g. hemolytic anaemia, aplastic anaemia, pure red cell anaemia and idiopathic thrombocytopenia), acquired hemophilia A, cold agglutinin disease, cryoglobulinemia, thrombotic thrombocytopenic purpura, Sjögren's syndrome, systemic lupus erythematosus, inflammatory muscle disorders, polychondritis, sclerodoma, anti-neutrophil cytoplasmic antibody-associated vasculitis, IgM mediated neuropathy, opsoclonus myoclonus syndrome, Wegener granulomatosis, dermatomyositis, chronic active hepatitis, myasthenia gravis, psoriasis, Steven-Johnson syndrome, pemphigus vulgaris, pemphigus foliacius, idiopathic sprue, autoimmune inflammatory bowel disease (including e.g. ulcerative colitis, Crohn's disease and Irritable Bowel Syndrome), endocrine ophthalmopathy, Graves' disease, sarcoidosis, multiple sclerosis, neuromyelitis optica, primary biliary cirrhosis, juvenile diabetes (diabetes mellitus type I), uveitis (anterior, intermediate and posterior as well as panuveitis), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy), tumors, inflammatory disease of skin and cornea, myositis, loosening of bone implants, metabolic disorders, such as atherosclerosis, diabetes, and dislipidemia.

The antibodies of the invention are also useful for the treatment, prevention, or amelioration of asthma, bronchitis, pneumoconiosis, pulmonary emphysema, and other obstructive or inflammatory diseases of the airways.

The antibodies of the invention are also useful for treating diseases of bone metabolism including osteoarthritis, osteoporosis and other inflammatory arthritides, and bone loss in general, including age-related bone loss, and in particular periodontal disease.

Since BAFFR binding to human peripheral blood lymphocytes and to the human B-cell line is mediated by BAFFR polypeptides, the antibodies of the invention may also be useful in diagnosing or treating B-cell neoplasms. Examples of such diseases and conditions include, but are not limited to, B-cell Non-Hodgkin's lymphomas, such as small lymphocytic lymphoma, lymphoplasmacytoid lymphoma, mantle cell lymphoma, follicular lymphoma, mucosa-associated lymphoid tissue lymphoma, diffuse large cell lymphoma, and Burkitt's lymphoma; precursor B-lymphoblastic leukemia; and B-cell chronic lymphocytic leukemia, and multiple myeloma. Other B-cell neoplasms are encompassed within the scope of the invention.

The antibodies of the invention may be administered as the sole active ingredient or in conjunction with, e.g. as an adjuvant to or in combination to, other drugs e.g. immunosuppressive or immunomodulating agents or other anti-inflammatory agents or other cytotoxic or anti-cancer agents, e.g. for the treatment or prevention of diseases mentioned above. For example, the antibodies of the invention may be used in combination with DMARD, e.g. Gold salts, sulphasalazine, antimalarias, methotrexate, D-penicillamine, azathioprine, mycophenolic acid, cyclosporine A, tacrolimus, sirolimus, minocycline, leflunomide, glucocorticoids; a calcineurin inhibitor, e.g. cyclosporin A or FK 506; a modulator of lymphocyte recirculation, e.g. FTY720 and FTY720 analogs; an mTOR inhibitor, e.g. rapamycin, 40-O-(2-hydroxyethyl)-rapamycin, CC1779, ABT578, AP23573 or TAFA-93; an ascomycin having immuno-suppressive properties, e.g. ABT-281, ASM981, etc.; corticosteroids; cyclo-phos-phamide; azathioprene; methotrexate; mizoribine; mycophenolic acid; myco-pheno-late mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD11a, CD25, CD28, CD40. CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; anti TNF agents, e.g. monoclonal antibodies to TNF, e.g. infliximab, adalimumab, CDP870, or receptor constructs to TNF-R1 or TNF-R11, e.g. Etanercept, PEG-TNF-R1; blockers of proinflammatory cytokines, IL-1 blockers, e.g. Anakinra or IL-1 trap, AAL160, ACZ 885, IL-6 blockers; chemokines blockers, e.g inhibitors or activators of proteases, e.g. metalloproteases, anti-IL4 antibodies, anti-IL-15 antibodies, anti-IL-6 antibodies, anti-IL-21 antibodies, anti-IL-12 antibodies, anti-p40 antibodies, anti-IL-17 antibodies, anti-CD20 antibodies, NSAIDs, such as aspirin or an anti-infectious agent (list not limited to the agent mentioned).

In accordance with the foregoing the present invention provides in a yet further aspect:

A method as defined above comprising co-administration, e.g. concomitantly or in sequence, of a therapeutically effective amount of a BAFFR antagonist, e.g., an antibody of the invention, and at least one second drug substance, said second drug substance being a immuno-suppressive/immunomodulatory, anti-inflammatory chemotherapeutic or anti-infectious drug, e.g. as indicated above.

Or, a therapeutic combination, e.g. a kit, comprising of a therapeutically effective amount of a) an BAFFR antagonist, e.g. an antibody of the invention, and b) at least one second substance selected from a immuno-suppressive/immunomodulatory, anti-inflammatory chemotherapeutic or anti-infectious drug, e.g. as indicated above. The kit may comprise instructions for its administration.

Where the antibodies of the invention are administered in conjunction with other immuno-suppressive/immunomodulatory, anti-inflammatory chemotherapeutic or anti-infectious therapy, dosages of the co-administered combination compound will of course vary depending on the type of co-drug employed, e.g. whether it is a DMARD, anti-TNF, IL-1 blacker or others, on the specific drug employed, on the condition being treated and so forth.

In one specific embodiment, the antibodies of the invention may be administered in combination with another B-cell killing agent, i.e., e.g, a CD20 targeting antibody with ADCC activity, such as Rituximab.

In other embodiment, the antibodies of the invention are administered only to patient population which is selected among patients suffering from SLE or RA and exhibiting an abnormal serum level of BLyS. In other embodiment, the antibodies of the invention are administered only to patient population which are selected among group of patients which respond to anti-BLyS treatment. Biomarkers that identify patients that have an increased likelihood of responding to anti-BLyS treatment may be any of the following without being limited to these: elevated levels of serum BLyS, elevated levels of certain B cell subsets, presence or absence of certain types of auto-antibodies.

In one embodiment, the antibodies of the invention can be used to detect levels of BAFFR, or levels of cells that contain BAFFR. This can be achieved, for example, by contacting a sample (such as an in vitro sample) and a control sample with the anti-BAFFR antibody under conditions that allow for the formation of a complex between the antibody and BAFFR. Any complexes formed between the antibody and BAFFR are detected and compared in the sample and the control. For example, standard detection methods, well known in the art, such as ELISA and flow cytometric assays, can be performed using the compositions of the invention.

Accordingly, in one aspect, the invention further provides methods for detecting the presence of BAFFR (e.g., human BAFFR antigen) in a sample, or measuring the amount of BAFFR, comprising contacting the sample, and a control sample, with an antibody of the invention, or an antigen binding region thereof, which specifically binds to BAFFR, under conditions that allow for formation of a complex between the antibody or portion thereof and BAFFR. The formation of a complex is then detected, wherein a difference in complex formation between the sample compared to the control sample is indicative of the presence of BAFFR in the sample.

Also within the scope of the invention are kits consisting of the compositions (e.g., antibodies, human antibodies and bispecific molecules) of the invention and instructions for use. The kit can further contain a least one additional reagent, or one or more additional antibodies of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit. The kit may further comprise tools for diagnosing whether a patient belongs to a group that responds to an anti-BAFFR antibody treatment, as defined above.

The invention having been fully described, it is further illustrated by the following examples and claims, which are illustrative and are not meant to be further limiting.

EXPERIMENTAL PARTS

Figure 1:
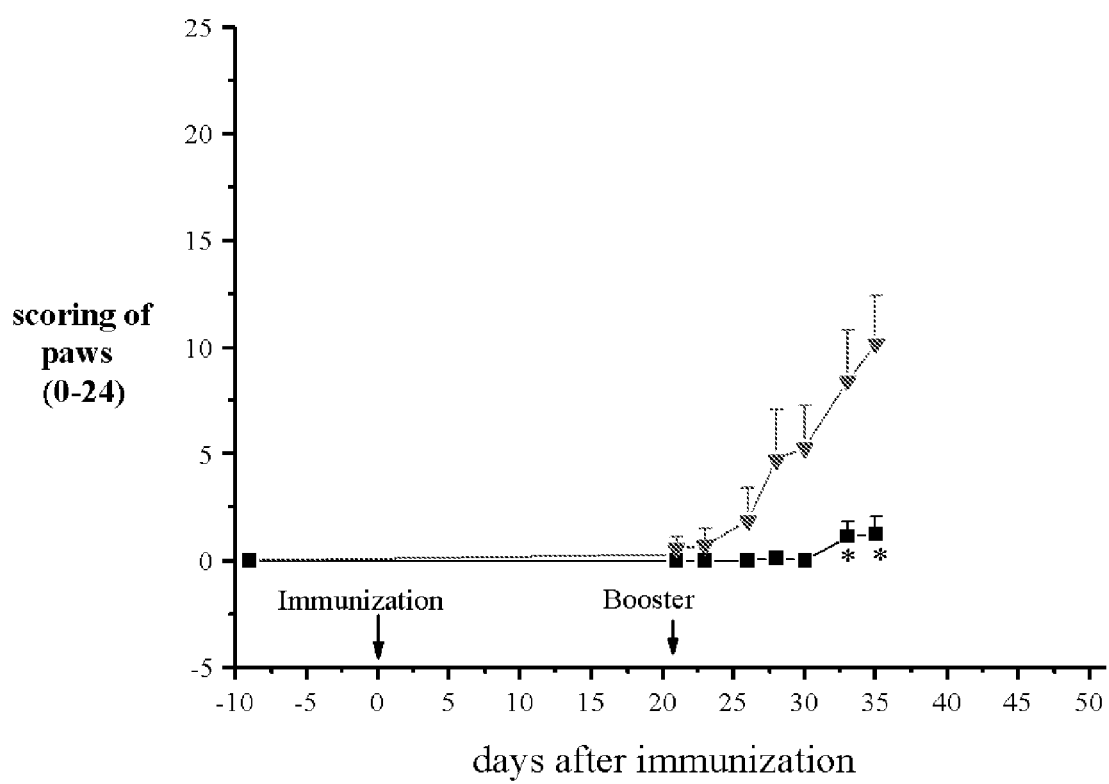
FIG. 1 shows the results of Collagen-induced arthritis (CIA) in DBA/1 mice (MCOL37) after immunization at day 0, Booster at day 21, and Treatment starting day minus 9. The square symbols show the paws scoring for Anti-BAFF Ab-MOR6743-mIgG2a with a dose equal to 200 µg/200 µl i.p. 2× a week, (n=8). The triangle symbols shows the paws scoring for an Isotype Anti CSA-IgG2a control with a dose equal to 200 µg/200 µl i.p. 2× a week, (n=7). Statistics: Dunnett Multiple Comparisons Test (One-way ANOVA). Compared with the Vehicle control (p<0.05*, p<0.01**, p>0.05n.s.).

1. Screening Assays
FACS Screening of Initial Pannings

For the detection of BAFFR binding Fab antibodies from first primary screening, e.g., phage display screening and/or for the secondary screening process of ELISA positive clones, lysates of selected *E. coli* clones can be screened in FACS as follows:

Cells of the respective cell line (parental cells or cells transfected with BAFFR) are counted and adjusted to 2×10$^7$ cells/ml in PBS/3% FCS/0.02% NaN$_3$ (FACS buffer). In a 96-well round bottom plate, 2×10$^5$ cells are mixed with 35 µl Fab-containing 1 bacterial lysate in a final volume of 100 µl FACS buffer and incubated on a shaker at 4° C. for one hour. Cells are then washed once with FACS buffer and resuspended in phycoerythrin-conjugated goat anti-human IgG secondary antibody which has been diluted 1:200 in FACS buffer. After one hour incubation at 4° C. on a shaker, cells were again washed once with FACS buffer, resuspended in FACS buffer and cell surface binding is measured, for example, via fluorescence intensity of the cells in the FACSArray instrument (Becton Dickinson).

Fc Capture ELISA

To identify BAFFR binding Fab antibodies in the enriched clones from phage display, lysates of selected *E. coli* clones are screened in an Fc capture ELISA setting as follows: Maxisorp 384-well plates are coated with 20 µg/ml goat anti-human IgG Fc diluted in PBS overnight at 4° C. On the next day, the plates are washed, blocked with 5% MTBST, and incubated with 5 µg/ml BAFFR:Fc (Alexis) for one hour at room temperature. In parallel, the Fab containing bacterial lysates are blocked with a final concentration of 2.5% milk powder. Then, pre-blocked bacterial lysates are added to the captured BAFFR:Fc on the plates. Subsequently BAFFR:Fc binding Fabs are detected by incubation with alkaline phosphatase conjugated goat anti-human IgG, Fab specific, diluted 1:5000 in 0.5% MPBST, followed by addition of AttoPhos fluorescence substrate (Roche Diagnostics). Fluorescence emission at 535 nm is recorded with excitation at 430 nm in a TECAN Spectrafluor plate reader.

Fab Capture ELISA

For the detection of BAFFR binding Fab antibodies from phage display, lysates of selected *E. coli* clones are screened in a Fab capture ELISA setting: Maxisorp 384-well plates are coated with a sheep anti-human IgG, Fd fragment specific antibody diluted 1:1000 in PBS overnight at 4° C. On the next day, the plates are washed and blocked with TBS/0.05% Tween/5% milk powder (5% MTBST) for one hour at room temperature. In parallel, the Fab containing bacterial lysates are blocked with a final concentration of 2.5% milk powder. Then, pre-blocked bacterial lysates are added to the capture antibody immobilized on the plates. Subsequently the captured HuCAL®-Fab fragments are allowed to bind to 1 µg/ml biotinylated BAFFR:Fc (diluted in PBST) which is finally detected by incubation with Streptavidin conjugated to alkaline phosphatase (Zymax), diluted 1:3000 in 2.5% MPBST, followed by addition of AttoPhos fluorescence substrate (Roche Diagnostics). Fluorescence emission at 535 nm was recorded with excitation at 430 nm in a TECAN Spectrafluor plate reader.

BAFFR-BLyS binding ELISA

To directly identify inhibitory antibodies, FLAG-tagged Fabs are screened in a BAFFR-BLyS binding ELISA: MaxiSorp 96-well plates are coated with 1 μg/ml hsBLyS in PBS, overnight at 4° C. On the next day, the plates are washed and blocked with PBS/2% BSA for at least one hour at room temperature. In parallel, the Fab containing bacterial lysates are blocked with a final concentration of 2.5% BSA. The pre-blocked bacterial lysates were incubated with 5 μg/ml monoclonal anti-FLAG M2 antibody for 30 min in order to increase the inhibitory activity by cross-linking and subsequently 10 ng/ml biotinylated BAFFR:Fc (diluted in PBS/2% BSA) are added for another 30 min at room temperature, slightly shaking. The pre-incubated lysate/bio-BAFFR:Fc mixture is added to plate-bound hsBLyS. After 30 min at room temperature and washing, the BLyS bound bio-BAFFR:Fc is detected by incubation with Streptavidin conjugated to alkaline phosphatase (Zymax) diluted 1:3000 in PBS/2.5% BSA, followed by addition of AttoPhos fluorescence substrate (Roche Diagnostics). Fluorescence emission at 535 nm was recorded with excitation at 430 nm in a TECAN Spectrafluor plate reader.

In case purified Fabs are used instead of bacterial lysates, the anti-FLAG cross-linking step is omitted.

FACS Screening after Maturation

Second Maturation:

For the screening of binders from the maturation the FACS analysis can be performed as described with the following changes: the lysate of the selected *E. coli* clones is diluted until maximum signals are below saturation. The lysates are analyzed for binding to Raji cells. $5 \times 10^4$ cells per 96-well are mixed with 100 μl of the different diluted bacterial lysates. The detection of the cell-bound Fabs is performed as described. Clones can be ranked according to their signal strength.

2. Affinity Determination of Antibodies Identified from Screening Assays

Solution Equilibrium Titration (SET) Method for KD Determination Using BioVeris

Affinity determination in solution can be basically performed as described in the literature (Friquet et al. (1985) J. Immunol. Meth. 77, 305-319 and Haenel et al. (2005) Anal. Biochem. 339, 182-184). In order to improve the sensitivity and accuracy of the SET method, the method is transferred from classical ELISA to ECL based BioVeris technology. 1 mg/ml goat-anti-human (Fab)$_2$ or goat-anti-mouse IgG, Fc fragment specific antibodies (Dianova) were labelled with BV-tag™ NHS-Ester (Bioveris Europe, Witney, Oxfordshire, UK) according to the manufacturer's instructions. The experiment is carried out in polypropylene microliter plates and PBS pH 7.4 supplemented with 0.5% BSA and 0.02% Tween 20 as assay buffer. Unlabeled BAFFR:Fc is diluted in 2n series. Wells without antigen were used to determine Smax values. After addition of 100 pM Fab (final concentration in 75 μl final volume), the mixture was incubated for 2 hours at RT. Subsequently a mixture of 25 μl Dynabeads (0.4 mg/ml M-280 Streptavidin, DYNAL, Hamburg), coated with 0.25 μg/ml biotinylated BAFFR:Fc antigen and BV-tag labeled detection antibody in a final dilution of 1:4000 for anti-human Fab or 1:2000 for anti-mouse IgG were added per well. After incubation for 30 min on an Eppendorf shaker (700 rpm) at RT, electrochemiluminescence signals are detected using a M-384 SERIES® Workstation (Bioveris Europe).

Biacore $K_D$ Determination on Directly Coated Antigen

The kinetic constants $k_{on}$ and $k_{off}$ are determined with serial dilutions of the respective Fab binding to either Fc-captured BAFFR:Fc or to covalently immobilized BAFFR:Fc (Alexis) or BAFFR (Peprotech) using the BIAcore 3000 instrument (Biacore, Uppsala, Sweden). For covalent immobilization of the antigens or the anti-Fc capture antibody standard EDC-NHS amine coupling chemistry is used. Kinetic measurements were done in PBS (136 mM NaCl, 2.7 mM KCl, 10 mM Na$_2$HPO$_4$, 1.76 mM KH$_2$PO$_4$ pH 7.4) at a flow rate of 20 μl/min using Fab concentrations ranging from 1.5 to 500 nM. The injection time for each concentration is 1 min, followed by either 3 or 15 min dissociation phase. For regeneration two injections of Glycine/HCl pH 1.5 are applied. All sensograms are fitted using the BIA evaluation software 3.1 (Biacore).

For affinity determination in presence of 10% human serum the kinetic measurement is performed in PBS containing 10% human serum which was sterile filtered (pore size 1.2 and 0.2 μm) prior to use in order to remove protein aggregates after thawing.

Determination of IC$_{50}$ Values in the BAFFR-BLyS Binding Assay (Competition FACS)

The BAFFR-BLyS binding assay is performed using Raji cells expressing endogenous BAFFR. The BAFFR specific Fabs are used in final dilutions ranging from 40 to 0.001 nM. The diluted Fabs are incubated in 96-well plates with $5 \times 10^4$ Raji cells per well for 1 h at 4° C. on a shaker. Then biotinylated hsBLyS is added in a final concentration of 25 ng/ml and the cells were incubated for 30 min at 4° C. on a shaker. The cells are washed twice with FACS buffer and then resuspended in phycoerythrin-conjugated Streptavidin (Dianova) which has been diluted 1:200 in FACS buffer. The staining is performed for one hour at 4° C. on a shaker. Finally the cells are washed twice with FACS buffer, resuspended in FACS buffer and BLyS binding to cell surface BAFFR is detected via fluorescence cytometry in the FACSArray instrument (Becton Dickinson).

Determination of IC$_{50}$ Values in the BAFFR:Fc-BLyS Binding Assay (Competition ELISA)

96-well MaxiSorp plates are coated over night at 4° C. with human soluble BLyS. After coating, the wells were washed 4 times with PBS/0.05% Tween20 (PBST) and then blocked for 1 h at 37° C. with PBST containing 1% bovine serum albumin followed by 4 washing steps with PBST. Biotinylated human BAFFR:Fc fusion protein (Axxora) at 20 ng/ml was added and captured for 1 h at 37° C. together with increasing concentrations of anti-BAFFR antibodies. After another washing round, ExtrAvidin-Alkaline Phosphatase (Sigma) was added to the wells and incubated for 30 minutes at 37° C. The bound phosphatase was detected by adding a solution containing p-nitrophenyl phosphate in diethanolamin (Sigma). The color reaction was stopped after ca. 20 minutes with an equal volume of 2N sodium hydroxide and the absorbance was measured at 405 nm on a plate reader (SpectraMax 190, Molecular Devices).

Determination of IC$_{50}$ Values in the BAFFR Peptide (miniBR3)-BLyS Binding Assay (Competition ELISA)

96-well MaxiSorp plates are coated over night at 4° C. with human soluble BLyS. After coating, the wells were washed 4 times with PBS/0.05% Tween20 (PBST) and then blocked for 1 h at 37° C. with PBST containing 1% bovine serum albumin followed by 4 washing steps with PBST. Biotinylated BAFFR derived peptide (miniBR3, PiCHEM, Austria) at 20 ng/ml was added and captured for 1 h at 37° C. together with increasing concentrations of anti-BAFFR antibodies. After another washing round, ExtrAvidin-Alkaline Phosphatase (Sigma) was added to the wells and incubated for 30 minutes at 37° C. The bound phosphatase was detected by adding a solution containing p-nitrophenyl phosphate in diethanolamin (Sigma). The color reaction was stopped after ca. 20 minutes with an equal volume of 2N sodium hydroxide and the absorbance was measured at 405 nm on a plate reader (SpectraMax 190, Molecular Devices).

Analysis of Cross-Reactivity to Cynomolgus BAFFR

The cross-reactivity of the Fabs to cynomolgus BAFFR is tested in FACS titration analysis on cyno BAFFR transfected HEK293T cells. The final candidate Fabs are used in dilutions ranging from 177 nM to 0.001 nM. The diluted Fabs are incubated in 96-well plates with $5\times10^4$ cells per well for 1 h at 4° C. on a shaker. Then the cells are washed twice with FACS buffer and resuspended in phycoerythrin-conjugated goat anti-human IgG (Dianova) which has been diluted 1:200 in FACS buffer. The staining is performed for 1 h at 4° C. on a shaker. Finally, the cells are washed twice with FACS buffer and Fab binding is detected via fluorescence cytometry in the FACSArray instrument (Becton Dickinson).

Analysis of Cross-Reactivity to BCMA and TACI

FACS

The cross-reactivity of the Fabs to BCMA is tested in FACS titration analysis on BCMA transfected HEK293T cells: the Fabs are used in final concentrations ranging from high nM or even µM down to pM. The staining of the cells and the detection of Fab binding are performed as described.

Elisa 384-well MaxiSorp plates are coated over night at 4° C. with a goat anti-human IgG, Fc γ fragment specific capture antibody. After coating the wells were washed twice with PBS/0.05% Tween20 (PBST) and then blocked for 1 h at RT with PBST containing 5% milk powder followed by two washing steps with PBST. Recombinant BCMA and TACI Fc-fusion proteins are added and captured for 1 h at RT. Then the purified and diluted BAFFR specific Fabs are added and the plates are incubated for 1 h at RT. To detect the Fabs, an alkaline phosphatase (AP)-conjugated goat anti-human IgG, Fab specific is added and the plates are incubated for 1 h at RT. Following each incubation step the wells are washed five times with PBST. For the detection of the AP-conjugates, AttoPhos (Roche) is used according to the manufacturer's instructions. Fluorescence is measured using a TECAN Spectrafluor plate reader.

3. Cell-Based Functional Assays

BLyS Induced Co-Stimulation of Human B-Cell Proliferation

Untouched B-lymphocytes were purified from peripheral blood mononuclear cells by depletion of other cell types using the MACS B-Cell isolation kit II (Miltenyi Biotec). To induce B-cell proliferation, 100 µl containing $1\times10^5$ cells were seeded into round-bottom 96 well plates in five replicates. Human soluble BLyS was added at a concentration of 3 ng/ml together with 0.35% (vol/vol) beads coupled with anti-human IgM antibodies. To determine their inhibitory potencies, anti-BAFFR antibodies at different concentrations were added at different concentrations. For the determination of agonistic properties of anti-BAFFR antibodies, the cells were induced with 0.35% (vol/vol) beads coupled with anti-human IgM antibodies and increasing concentrations of anti-BAFFR antibodies (no additional BLyS added). Afterwards, the cells were cultured for 3 days. For the last 12 hours, 1 µCi/well of tritiated thymidine was added. Cells were harvested onto a filter and the cell associated radioactivity was quantified in a scintillation counter.

BLyS Induced Co-Stimulation of Human B-Cell IgG1 Production

Untouched B-lymphocytes were purified from peripheral blood mononuclear cells by depletion of other cell types using the MACS B-Cell isolation kit II (Miltenyi Biotec). To induce IgG1 synthesis, 100 µl containing $1\times10^5$ cells were seeded into round-bottom 96 well plates in five replicates and stimulated with 3 ng/ml human soluble BLyS together with 100 ng/mL human IL-21 (Pepro Tech Inc.). To determine their inhibitory potencies, anti-BAFFR antibodies were added at different concentrations. For the determination of agonistic properties of anti-BAFFR antibodies, the cells were induced with 100 ng/mL human IL-21 and increasing concentrations of anti-BAFFR antibodies (no additional BLyS added). The cells were cultured for 9 days and the supernatants were collected. IgG1 was determined in the cell supernatants by enzyme linked immuno-sorbent assay (ELISA).

Antibody Dependent Cellular Cytotoxicity Assay (ADCC)

Untouched B-lymphocytes were purified from peripheral blood mononuclear cells (PBMC) by depletion of other cell types using the MACS B-Cell isolation kit II (Miltenyi Biotec). Similarly, autologous natural killer (NK) cells were purified from PBMC by negative depletion on an AutoMACs device using the MACS human NK Cell Isolation Kit (Milteny Biotech). Increasing concentrations of anti-BAFFR antibodies in 100 µl were incubated with $1\times10^4$ B-cells in 50 µl of culture medium in V-shaped 96-well plates (Corning) for 20 minutes. Then, 50 µl containing $1\times10^5$ NK cells were added and incubated for 4 hours at 37° C. The cells were spun down and 150 µl of supernatant was removed. The cells were re-suspended and 10 µl of a 1:100 dilution of 7-amino actinomycin D (7-AAD, Becton Dickinson) was added. The cells were enumerated in a FACScalibur (Becton Dickinson) instrument. Data analysis of 7-AAD positive cells was performed using the CellQuest Pro software (Becton Dickinson).

4. In Vivo Functional Assays

In Vivo B Cell Depleting Assay

Depleting effects of anti-BAFFR antibodies on B cell numbers are assessed as follows:
  a) Relative numbers of B cells in the blood lymphocyte compartment are measured by staining of whole blood or isolated peripheral blood mononuclear cells (PBMC) with fluorescent labelled antibodies specific for B cell and T cell surface markers (CD3 and CD19, respectively). The relative percentage of CD3 and CD19 positive cells is quantified by flow cytometry and a selective reduction of B cells can be expressed by an increase in the ratio of T cells to B cells.
  b) Absolute B cell numbers are determined as cells/microliter of blood by flow cytometry using fluorescent labelled anti-CD19 antibody in combination with Tru-COUNT tubes (Cat #340334; Becton Dickinson, San Jose Calif.) according to the manufacturer's instructions.

CIA Animal Model Assay

Collagen induced arthritis (CIA) has been proposed to reflect many aspects of the human disease. CIA is induced by immunisation of genetically susceptible strains of mice with type II collagen in adjuvant and is mediated by autoimmune reactions including autoantibody generation, which then bind to a particular region of type II collagen (CII). Both B- and T-lymphocytes are important in the pathogenesis of CIA. The joint histology in the animal model has many similarities to the human disease with aspects such as synovial hyperplasia, marginal erosion and destruction of the cartilage surface being some of the features of the pathophysiology.

After immunization with collagen type II (C-II) at day 0 and subsequent booster treatment with C-II at day 21, DBA/1 mice usually develop severe symptoms of arthritis. In the present study, the mice are treated intraperitoneally, twice weekly with 200 ug per mouse of anti BAFFR antibodies or isotype control antibodies in a prophylactic regimen (days minus 10 to approximately day 36). Paw swelling is monitored throughout the experiment as an indicator of disease severity. Histology is performed on the paws at the end of the experiment if swelling efficacy is observed. B cell depletion in spleen, blood and lymph nodes can be assessed by cell isolation and FACS analysis. ELISA for anti collagen antibodies are performed to investigate whether the antibody titre also is suppressed. Antibodies are presumed to have good efficacy in a CIA animal model if they exhibit a statistically significant reduction in swelling when a Dunnetts multiple comparison test (ONE WAY ANOVA) has been applied. Usually this translates to a 50% reduction in paw swelling over the time course with low variation between animals within each group.

EXAMPLES

The following table describes SEQ ID numbers for the corresponding CDRs of specific examples of antibodies of the invention. HCDR1, HCDR2 and HCDR3 stands for the CDR1, CDR2 and CDR3 of the heavy chain of an antibody and LCDR1, LCDR2 and LCDR3 stands for the CDR1, CDR2 and CDR3 of the light chain of an antibody.

TABLE 1

Correspondence mAb# and SEQ IDs

| mAb # | HCDR1 | HCDR2 | HCDR3 | LCDR1 | LCDR2 | LCDR3 |
|---|---|---|---|---|---|---|
| MOR06743 | NO: 2 | NO: 9 | NO: 16 | NO: 23 | NO: 30 | NO: 37 |
| MOR06654 | NO: 3 | NO: 10 | NO: 17 | NO: 24 | NO: 31 | NO: 38 |
| MOR07342 | NO: 4 | NO: 11 | NO: 18 | NO: 25 | NO: 32 | NO: 39 |
| MOR07347 | NO: 5 | NO: 12 | NO: 19 | NO: 26 | NO: 33 | NO: 40 |
| MOR07348 | NO: 6 | NO: 13 | NO: 20 | NO: 27 | NO: 34 | NO: 41 |
| MOR07349 | NO: 7 | NO: 14 | NO: 21 | NO: 28 | NO: 35 | NO: 42 |

Detailed Characterization of the Examples

Determination of the EC50 of the Antibodies of the Invention in a Human Fab Format in FACS The $EC_{50}$ of the Fabs is determined by Fab titration in FACS on transfected HEK293 cells as well as on Raji cells expressing endogenous BAFFR.

TABLE 2

$EC_{50}$ of Fab antibodies on Raji cells and transfected HEK293-hBAFFR

| MOR0 | $EC_{50}$ [nM] on Raji cells | $EC_{50}$ [nM] on HEK293-hBAFFR |
|---|---|---|
| 6654 | 0.12/0.32/0.44/0.51 | 0.98/0.25 |
| 6743 | 0.23/0.18 | 0.59/0.27 |
| 7342 | 0.06 | 0.18 |
| 7347 | 0.03/0.06/0.18 | 0.08 |
| 7348 | 0.12 | 0.24 |
| 7349 | 0.13 | 0.24 |

Since the Glutamine found in MOR07347 at position 110 in HCDR3 seems to be advantageous, this position is also introduced in the cross-clone MOR6743 resulting in the antibody MOR07685. This antibody shows an $EC_{50}$ value determined in FACS titration that is comparable to those of MOR06743 and MOR07347.

Determination of $IC_{50}$ Values of the Fabs in BAFFR-BLyS Binding Assay (FACS)

The IC50 values of the antibodies of the invention in a human Fab format are determined in a BAFFR-BLyS binding inhibition assay by Fab titration on Raji cells (FACS). The results from these analyses are listed in Table 3.

TABLE 3

$IC_{50}$ values for BAFFR - BLyS binding inhibition in a human Fab format on Raji cells

| MOR0 | $IC_{50}$ [nM] |
|---|---|
| 6654 | 0.09/0.37/0.30/0.16 |
| 6743 | 0.13/0.17 |
| 7342 | 0.09 |
| 7347 | 0.02 |
| 7348 | 0.20 |
| 7349 | 0.17 |
| 7685 | 0.12 |

Determination of $IC_{50}$ Values of the Antibodies in BAFFR-BLyS Binding Assays (ELISA)

The IC50 values of the antibodies of the invention in a human Fab and IgG2 format are determined in a competitive ELISA in which the antibodies are titrated to inhibit the interaction between the extracellular domain of BAFFR (BAFFR:Fc fusion protein) and human soluble BLyS. $IC_{50}$ values were also determined in a similar competitive ELISA in which the antibodies of the invention were titrated to inhibit the binding of a BAFFR derived peptide (miniBR3) to human soluble BLyS assay.

The results from these analyses are listed in Table 4.

TABLE 4

$IC_{50}$ values for BAFFR - BLyS binding inhibition in a human IgG2 format

| | BLyS/BAFFR:Fc competition ELISA $IC_{50}$ [nM] | | BLyS/BAFFR peptide competition ELISA $IC_{50}$ [nM] |
|---|---|---|---|
| MOR0 | Hu Fab | Hu IgG2 | Hu IgG2 |
| 6654 | 1.1 | 0.024 | 5.9 |
| 6743 | 0.1 | 0.034 | 3.5 |
| 7342 | 0.14 | n.d. | n.d. |
| 7347 | 0.1 | 0.019 | n.d. |
| 7348 | 0.96 | n.d. | n.d. |
| 7349 | 0.44 | 0.05 | n.d. |

Analysis of Cross-Reactivity to BCMA and TACI

BCMA and TACI are proteins that are related to BAFFR and can also bind the ligand BLyS. The Fabs are tested for unwanted cross-reactivity to these two proteins. The cross-reactivity of the binders to BCMA is tested on recombinant protein in ELISA and on cell surface antigen in FACS analysis.

In ELISA the Fabs are titrated from 400 nM down to 0.005 nM on BAFFR:Fc captured to a Maxisorp plate via an anti-human Fc antibody. Only MOR07342 and MOR07346 show some cross-reactivity to BCMA at high Fab concentrations >100 nM. In contrast MOR06654, MOR07347, MOR07348, MOR07349 show no binding to BCMA above background. A 1000-fold discrimination factor is met by all Fabs.

In FACS the following Fabs are analyzed on BCMA-transfected HEK293 cells and titrated from 1 µM down to 0.005 nM: MOR06654, MOR06743, MOR07342, MOR07347, MOR7348 and MOR07349. At 330 nM only MOR07342 show an elevated binding signal which is 2-fold over background. All other tested Fabs show no signal at this concentration. At a Fab concentration of 1 µM MOR06654, MOR06743 and MOR07347 showed signals 3-4 fold over background. MOR07342 shows binding to BCMA-transfected cells with a signal 20-fold over background. MOR007348 and MOR07349 do not bind at all to BCMA up to a Fab concentration of 1 µM.

Potency of Antibodies of the Invention in Functional B Cell Assays

Potency and Agonism of Antibodies in the BLyS Mediated Co-Stimulatory B-Cell Proliferation Assay Primary human blood derived B-cells are stimulated with anti-IgM antibodies and human soluble BLyS to induced B-cell proliferation. Antibodies of the invention are titrated to block the co-stimulatory effect of BLyS. In order to measure the agonistic (i.e. BLyS-like) effects of the antibodies, B-cells are stimulated with anti-IgM antibodies alone. BAFFR antibodies are titrated to measure a potential enhancement of B-cell proliferation. The results from these analyses are shown in Table 5 for different BAFFR antibody formats (human Fab, IgG2 and IgG1).

TABLE 5 antagonistic and agonistic activity of antibodies of the invention in a Fab, IgG2 and IgG1 format

| | | B-cell proliferation | |
| --- | --- | --- | --- |
| format | MOR0 | Inhibition $IC_{50}$ [nM] | Agonism $EC_{50}$ [nM] |
| Fab | 6654 | 16 | >187 |
| Fab | 6743 | 2 | >187 |
| Fab | 7342 | 0.9 | >187 |
| Fab | 7347 | 1.3 | >187 |
| Fab | 7348 | 2.9 | >187 |
| Fab | 7349 | 3.5 | >187 |
| IgG2 | 6654 | 0.084 | >187 |
| IgG2 | 6743 | 0.032 | >187 |
| IgG2 | 7342 | 0.041 | >187 |
| IgG2 | 7347 | 0.043 | >187 |
| IgG2 | 7348 | 0.079 | >187 |
| IgG2 | 7349 | 0.072 | >187 |
| IgG1 | 6654 | 0.122 | >187 |
| IgG1 | 7342 | 0.031 | >187 |
| IgG1 | 7347 | 0.034 | >187 |
| IgG1 | 7349 | 0.079 | >187 |

Potency and Agonism of Antibodies in the BLyS Mediated Co-Stimulatory B-Cell IgG1 Production Assay Primary human blood derived B-cells are stimulated with IL-21 and human soluble BLyS to induce IgG1 production. Antibodies of the invention are titrated to block the co-stimulatory effect of BLyS. In order to measure the agonistic (i.e. BLyS-like) effects of the antibodies, B-cells are stimulated with IL-21 alone. Anti-BAFFR antibodies are titrated to measure a potential enhancement of IgG1 secretion. The results from these analyses are shown in Table 6.

TABLE 6

$IC_{50}$ of B-cell IgG1 production

| | | B-cell IgG1 production | |
| --- | --- | --- | --- |
| format | MOR0 | Inhibition $IC_{50}$ [nM] | Agonism $EC_{50}$ [nM] |
| IgG2 | 6654 | 0.028 | >62.5 |
| IgG2 | 6743 | 0.018 | >62.5 |
| IgG2 | 7342 | 0.023 | >62.5 |
| IgG2 | 7347 | 0.024 | >62.5 |
| IgG2 | 7348 | 0.088 | >62.5 |
| IgG2 | 7349 | 0.039 | >62.5 |

Potency of Antibodies to Elicit B-Cell Killing in the ADCC Assay

Anti-BAFFR antibodies in increasing concentrations are allowed to bind to primary human blood derived B-cells before autologous natural killer (NK) cells are added to induce the killing reaction. After four hours, the number of apoptotic cells is enumerated by FACS. The results from these analyses are shown in Table 7 for IgG1 and IgG2 antibody formats.

TABLE 7

$EC_{50}$ showing B-cell killing activity of antibodies of the invention in IgG1 and IgG2 format

| format | MOR0 | ADCC $EC_{50}$ [nM] |
| --- | --- | --- |
| IgG2 | 6654 | >63 |
| IgG2 | 7342 | >63 |
| IgG1 | 6654 | 0.186 |
| IgG1 | 7342 | 0.195 |

Example 2

In Vivo Efficacy in a CIA Mouse Model

Mice were treated with 200 ug/animal of anti BAFFR antibody (conjugated to murine IgG2a) or isotype control antibody 9, 6 and 2 days before immunization with bovine type 2 collagen in complete Freunds adjuvant. Antibodies were applied at 200 ug/mouse twice a week, throughout the experiment (until day 35 after immunization). Mice were boosted with bovine type 2 collagen in phosphate buffered saline, 21 days after immunization. Swelling was assessed every 2 to 3 days from day of boost onwards. As shown in FIG. 1, anti BAFFR antibody significantly reduced swelling when compared to its control anti CSA antibody.

Example 3

Depletion of Peripheral B Cells in Cynomolgus Monkey

Figure 2:
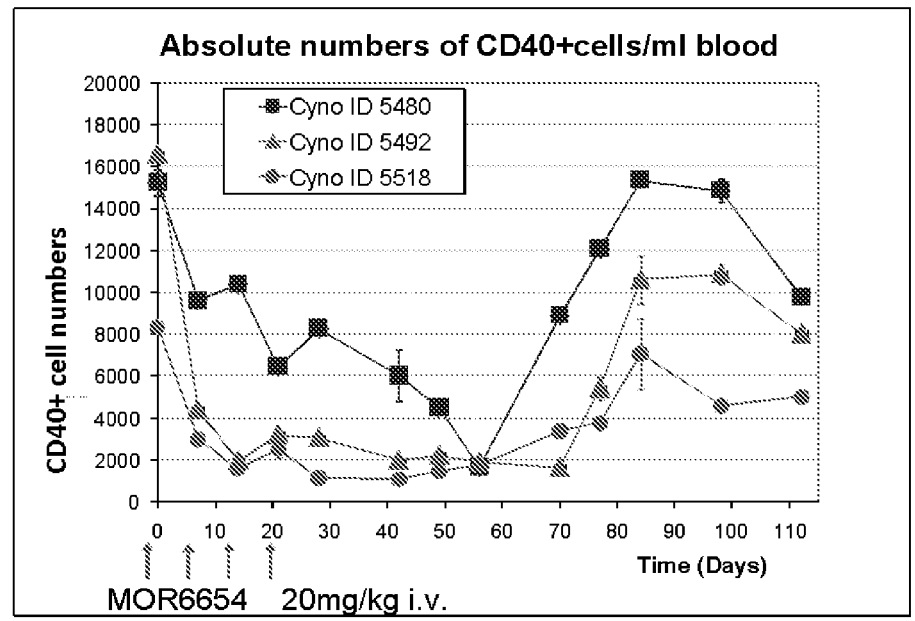
FIG. 2 shows the absolute number of CD20+ and CD40+ peripheral blood cells in 3 cynomolgous monkeys after 20 mg/kg intravenous administration of anti-BAFFR (MOR06654) antibodies.
Figure 2:
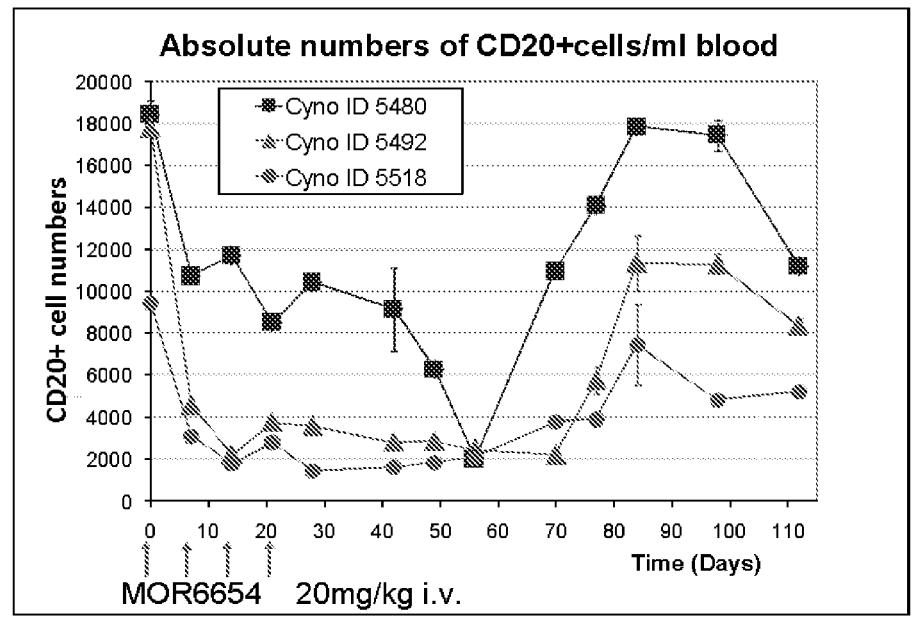

Cynomolgus monkeys were treated with 4 weekly doses of 20 mg/kg i.v. of the anti-human BAFF-R monoclonal antibody MOR06654 (IgG1/k). B cells numbers in blood were determined at different pre-dose and post dose time points by FACS analysis. In brief, blood samples were incubated with fluorescence-labelled anti-CD20 antibody (Anti-human CD20-PE, Clone 2H7, BD, cat#555623) or anti-CD40 antibody (Anti-human CD40-APC, Clone 5C3 BD, cat#555591) in True Count tubes (BD, cat#340334). The results are shown in FIG. 2.

B cells got rapidly depleted in treated monkeys down to a mean of 33% of the pre-dose B cell number (n=3). Reduction of B cells remained or increased with subsequent doses. The mean of B cell reduction was 85% (n=3) on day 56, i.e., 45 days after the last dose. A gradual increase of B cell numbers was observed after day 56.

In conclusion, treatment with the human anti-BAFF-R antibody leads to a rapid and sustained reduction in peripheral B cells in cynomolgus monkey. This pharmacodynamic effect is reversible, allow for the restoration of the normal B cell homeostasis after elimination of the antibody from circulation.

Example 4

Stronger and More Sustained B Cell Depletion with Non-Fucosylated Antibodies

In a second experiment, cynomolgus monkeys were treated with a single dose of MOR06654 (IgG1) or the non-fucosylated variant MOR06654B. MOR06654B was produced using the Potelligent™ cell lines (Biowa, Inc.). These cell lines are CHO mammalian cell lines, knocked-out for the gene encoding fucosyltransferase. The antibodies (MOR06654B) produced in such cell lines are not fucosylated. This time, the single dose was only 20 µg/kg i.v.

Figure 3A:
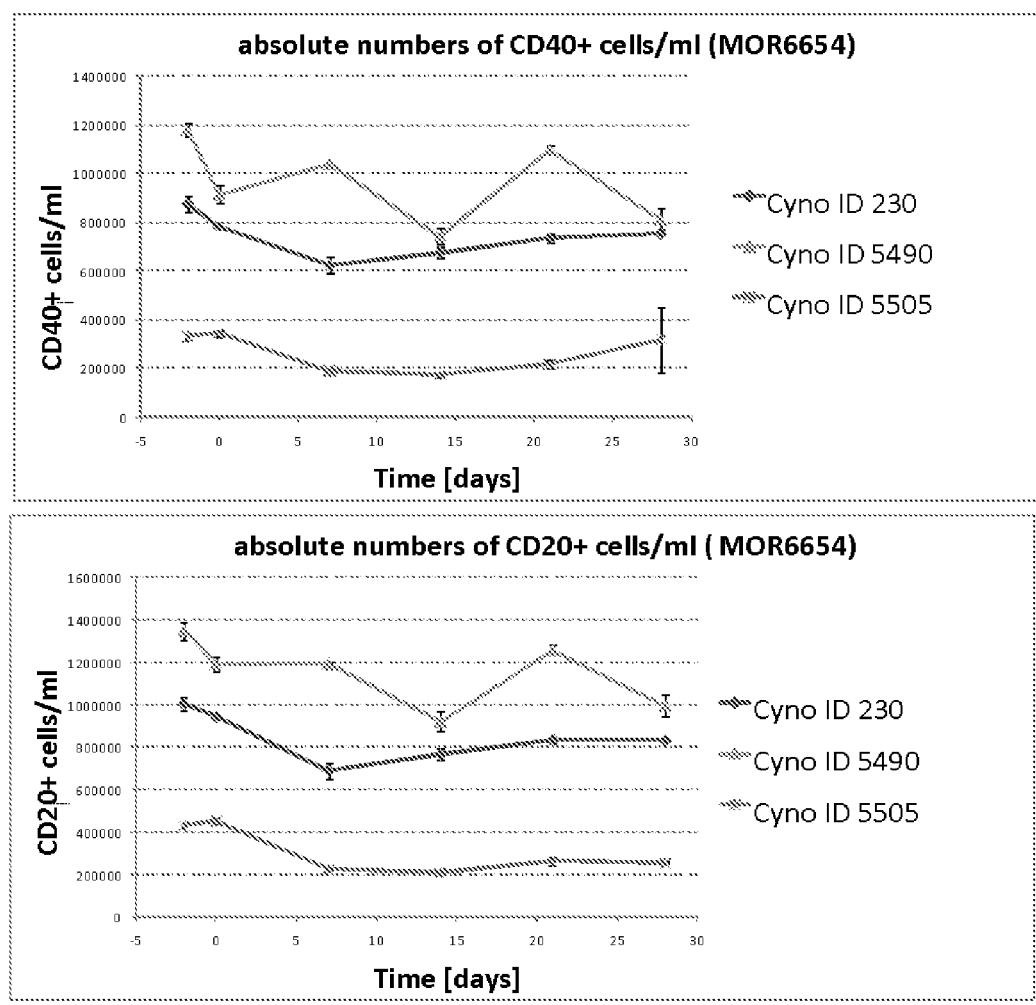
FIG. 3A shows the absolute number of CD20+ and CD40+ peripheral blood cells in 3 cynomolgous monkeys after 20 µg/kg intravenous administration of anti-BAFFR (MOR06654) antibodies.
Figure 3B:
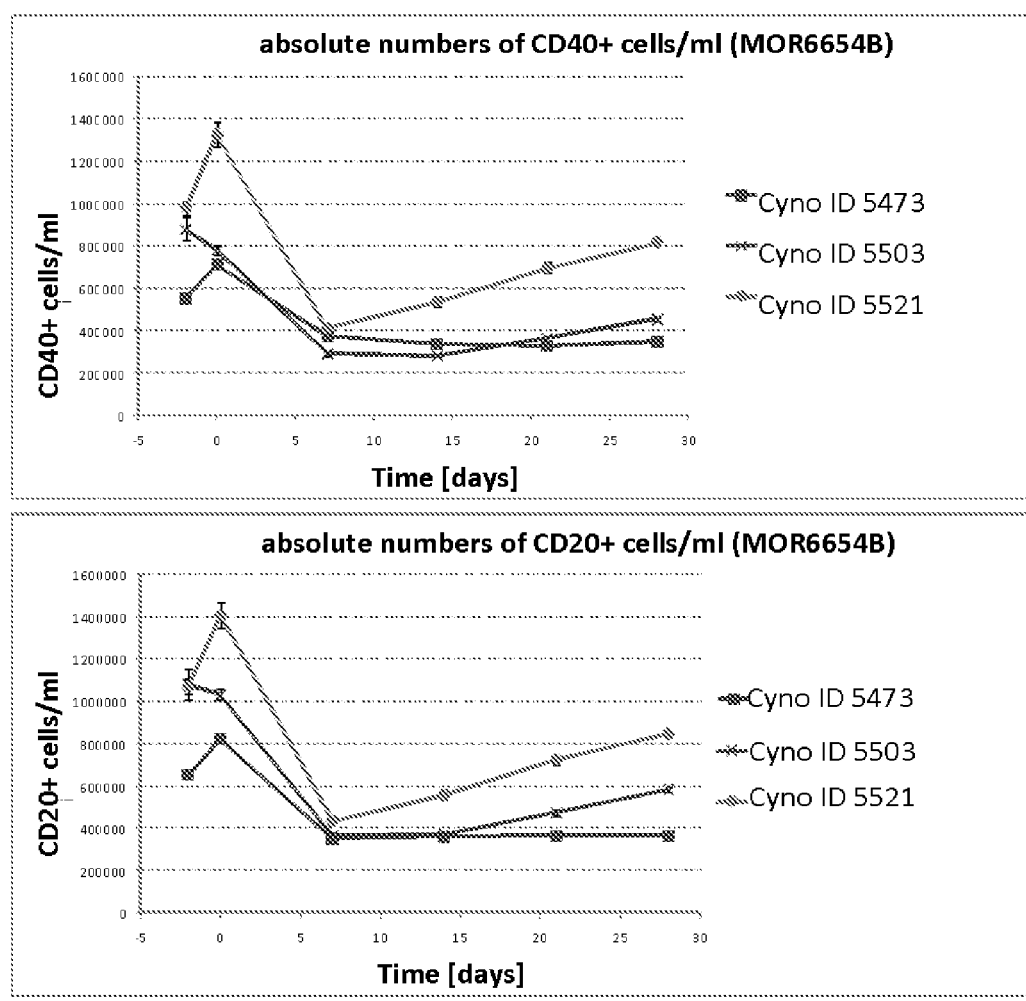
FIG. 3B shows the absolute number o CD20+ and CD40+ peripheral blood cells in 3 cynomolgous monkeys after 20 µg/kg intravenous administration of non-fucosylated anti-BAFFR (MOR06654) antibodies.

As shown in FIG. 3, a marginal, but observable reduction of B cells by treatment with 20 µg/kg i.v. MOR06654 was observed on day 7 (mean reduction 22%, n=3). The decrease in peripheral B cell was more pronounced and more sustained for the antibody MOR06654B, lacking fucose. Here the reduction reached 57% (n=3) and is still about 40% (n=3) 28 days after the single dose.

Example 5

Screening Antibodies that Cross-Block BAFFR Binding Antibodies of the Present Invention Biacore Cross-Blocking Assay The following generally describes a suitable Biacore assay for determining whether an antibody or other binding agent cross-blocks or is capable of cross-blocking antibodies according to the invention. It will be appreciated that the assay can be used with any of the BAFFR binding agents described herein.

The Biacore machine (for example the BIAcore 3000) is operated in line with the manufacturer's recommendations.

BAFFR may be coupled to e.g. a CM5 Biacore chip by way of routinely used amine coupling chemistry, e.g. EDC-NHS amine couplilng, to create a BAFFR-coated surface. In order to obtain measurable levels of binding, typically 200-800 resonance units of BAFFR may be coupled to the chip (this amount gives measurable levels of binding and is at the same time readily saturable by the concentrations of test reagent being used).

An alternative way of attaching BAFFR to the BIAcore chip is by using a "tagged" version of BAFFR, for example N-terminal or C-terminal His-tagged BAFFR. In this format, an anti-His antibody would be coupled to the Biacore chip and then the His-tagged BAFFR would be passed over the surface of the chip and captured by the anti-His antibody.

The two antibodies to be assessed for their ability to cross-block each other are mixed in a stoichiometrical amount, e.g. at a one to one molar ratio, of binding sites in a suitable buffer to create the test mixture. The buffer used is typically a buffer which is normally used in protein chemistry, such as e.g. PBS (136 mM NaCl, 2.7 mM KCl, 10 mM $Na_2HPO_4$, 1.76 mM $KH_2PO_4$, pH 7.4). When calculating the concentrations on a binding site-basis the molecular weight of an antibody is assumed to be the total molecular weight of the antibody divided by the number of target (i.e. BAFFR) binding sites on that antibody.

The concentration of each antibody in the test mixture should be high enough to ensure saturation of the binding sites for that antibody on the BAFFR molecules which are bound on the BIAcore chip. The antibodies in the mixture are at the same molar concentration (on a binding basis) and that concentration would typically be between 1.0mM and 1.5 mM (on a binding site basis).

Separate solutions containing the separate antibodies on their own are also prepared. The buffer used for these separate solutions should be the same buffer and at the same concentration as was used for the test mixture.

The test mixture is passed over the BAFFR-coated BIAcore chip and the binding recorded. The bound antibodies are thereafter removed by treating the chip with e.g. an acid, such as 30 mM HCl for about 1 minute. It is important that the BAFFR molecules which are bound to the chip are not damaged.

The solution of the first antibody alone is then passed over the BAFFR-coated surface and the binding is recorded. Thereafter, the chip is treated to remove all of the bound antibody without damaging the chip-bound BAFFR, e.g. by way of above mentioned acid treatment.

The solution of the second antibody alone is then passed over the BAFFR-coated surface and the amount of binding recorded.

The maximal theoretical binding can be defined as the sum of the binding to BAFFR of each antibody separately. This is then compared to the actual binding of the mixture of antibodies measured. If the actual binding is lower than that of the theoretical binding, the two antibodies are cross-blocking each other.

Elisa-Based Cross-Blocking Assay

Cross-blocking of an anti-BAFFR antibody or another BAFFR binding agent may also be detected by using an ELISA assay.

The general principle of the ELISA-assay involves coating an anti-BAFFR antibody onto the wells of an ELISA plate. An excess amount of a second, potentially cross-blocking, anti-BAFFR antibody is then added in solution (i.e. not bound to the ELISA plate). A limited amount of BAFFR-Fc is then added to the wells.

The antibody which is coated onto the wells and the antibody in solution will compete for binding of the limited number of BAFFR molecules. The plate is then washed to remove BAFFR-Fc that has not bound to the coated antibody and to also remove the second, solution phase, antibody as well as any complexes formed between the second, solution phase antibody and BAFFR-Fc. The amount of bound BAFFR is then measured using an appropriate BAFFR detection reagent. An antibody in solution that is able to cross-block the coated antibody will be able to cause a decrease in the number of BAFFR molecules that the coated antibody can bind relative to the number of BAFFR molecules that the coated antibody can bind in the absence of the second, solution phase, antibody.

This assay is described in more detail further below for two antibodies termed Ab-X and Ab-Y. In the instance where Ab-X is chosen to be the immobilized antibody, it is coated onto the wells of the ELISA plate, after which the plates are blocked with a suitable blocking solution to minimize non-specific binding of reagents that are subsequently added. An excess amount of Ab-Y is then added to the ELISA plate such that the moles of Ab-Y BAFFR binding sites per well are at least 10 fold higher than the moles of Ab-X BAFFR binding sites that were used, per well, during the coating of the ELISA plate. BAFFR-Fc is then added such that the moles of BAFFR-Fc added per well are at least 25-fold lower than the moles of Ab-X BAFFR binding sites that were used for coating each well. Following a suitable incubation period, the ELISA plate is washed and a BAFFR detection reagent is added to measure the amount of BAFFR specifically bound by the coated anti-BAFFR antibody (in this case Ab-X). The background signal for the assay is defined as the signal obtained in wells with the coated antibody (in this case Ab-X), second solution phase antibody (in this case Ab-Y), BAFFR buffer only (i.e. no BAFFR) and BAFFR detection reagents. The positive control signal for the assay is defined as the signal obtained in wells with the coated antibody (in this case Ab-X), second solution phase antibody buffer only (i.e.

no second solution phase antibody), BAFFR and BAFFR detection reagents. The ELISA assay needs to be run in such a manner so that the positive control signal is at least 6 times the background signal.

To avoid any artifacts (e.g. significantly different affinities between Ab-X and Ab-Y for BAFFR) resulting from the choice of which antibody to use as the coating antibody and which to use as the second (competitor) antibody, the cross-blocking assay needs to be run in two formats: 1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

The invention claimed is:

1. An isolated antibody or antigen-binding portion thereof comprising:
   (a) an HCDR1 comprising an amino acid sequence of SEQ ID NO: 3;
   (b) an HCDR2 comprising an amino acid sequence with amino acid substitutions at the $9^{th}$, $11^{th}$, or both the $9^{th}$ and $11^{th}$ amino acids of SEQ ID NO: 10;
   (c) an HCDR3 comprising an amino acid sequence with amino acid substitutions at the $2^{nd}$ or $12^{th}$ amino acids of SEQ ID NO: 17;
   (d) an LCDR1 comprising an amino acid sequence with amino acid substitutions at the $5^{th}$, $7^{th}$, $8^{th}$, $9^{th}$ or all of these amino acids of SEQ ID NO: 24,
   (e) an LCDR2 comprising an amino acid sequence of SEQ ID NO: 31;and
   (f) an LCDR3 comprising an amino acid sequence with amino acid substitutions at the $3^{rd}$, $8^{th}$, or both the $3^{rd}$ and $8^{th}$ amino acids of SEQ ID NO: 38;
   and wherein said antibody or antigen-binding portion thereof binds to the BAFFR polypeptide with a $K_D$ of 100 nM or less and inhibits BLyS induced human B cell proliferation with an $IC_{50}$ around 10 nM or less.

2. The isolated antibody or antigen-binding portion thereof, of claim 1 that depletes B cells in vivo and in vitro.

3. The isolated antibody or antigen-binding portion thereof, of claim 2, wherein said antibody or protein deletes B cells in vitro with an EC50 of 10 nM or less as measured in a human B cell depleting ADCC assay.

4. The isolated antibody or antigen-binding portion thereof, of claim 2 that is capable of reducing the percentage of B cells in vivo up to 90% as compared to untreated control, as measured by Fluorescent Activated Cell Sorting of B cells.

5. The isolated antibody or antigen-binding portion thereof, of claim 1, wherein said antibody or protein has no agonistic activity.

6. The isolated antibody or antigen-binding portion thereof, of claim 1, which is a fully human or humanized IgG1 antibody.

7. The isolated antibody or antigen-binding portion thereof, of claim 6, which comprises a mutated or chemically modified amino acid Fc region, wherein said mutated or chemically modified Fc region provides increased ADCC activity when compared with the wild type Fc region.

8. The isolated antibody or antigen-binding portion thereof, of claim 6, wherein said antibody or protein is hypofucosylated or non-fucosylated and has reduced amounts of or no fucosyl residues.

9. The isolated antibody or antigen-binding portion thereof, of claim 8, which is produced by recombinant expression in a cell line with deficient expression of the FUT8 gene encoding fucosyltransferase, thereby increasing ADCC activity of antibodies produced therein as compared with a cell line expressing the wild type FUT8 gene.

10. A composition comprising an antibody or antigen-binding portion, according to claim 1 and a pharmaceutically acceptable carrier.

* * * * *

SEQUENCE LISTING

```
<160> NUMBER OF SEQ ID NOS: 88

<210> SEQ ID NO 1
<211> LENGTH: 12
<212> TYPE: PRT
<213> ORGANISM: Homo sapiens

<400> SEQUENCE: 1

Gly Asp Ser Val Ser Ser Asn Ser Ala Ala Trp Gly
1               5                   10

<210> SEQ ID NO 2
<211> LENGTH: 12
<212> TYPE: PRT
<213> ORGANISM: Homo sapiens

<400> SEQUENCE: 2

Gly Asp Ser Val Ser Ser Asn Ser Ala Ala Trp Gly
1               5                   10

<210> SEQ ID NO 3
<211> LENGTH: 12
<212> TYPE: PRT
<213> ORGANISM: Homo sapiens

<400> SEQUENCE: 3

Gly Asp Ser Val Ser Ser Asn Ser Ala Ala Trp Gly
1               5                   10

<210> SEQ ID NO 4
<211> LENGTH: 12
<212> TYPE: PRT
<213> ORGANISM: Homo sapiens

<400> SEQUENCE: 4

Gly Asp Ser Val Ser Ser Asn Ser Ala Ala Trp Gly
1               5                   10

<210> SEQ ID NO 5
<211> LENGTH: 12
<212> TYPE: PRT
<213> ORGANISM: Homo sapiens

<400> SEQUENCE: 5

Gly Asp Ser Val Ser Ser Asn Ser Ala Ala Trp Gly
1               5                   10

<210> SEQ ID NO 6
<211> LENGTH: 12
<212> TYPE: PRT
<213> ORGANISM: Homo sapiens

<400> SEQUENCE: 6

Gly Asp Ser Val Ser Ser Asn Ser Ala Ala Trp Gly
1               5                   10
```

```
<210> SEQ ID NO 7
<211> LENGTH: 12
<212> TYPE: PRT
<213> ORGANISM: Homo sapiens

<400> SEQUENCE: 7

Gly Asp Ser Val Ser Ser Asn Ser Ala Ala Trp Gly
1               5                   10

<210> SEQ ID NO 8
<211> LENGTH: 18
<212> TYPE: PRT
<213> ORGANISM: Homo sapiens

<400> SEQUENCE: 8

Arg Ile Tyr Tyr Arg Ser Lys Trp Tyr Asn Asp Tyr Ala Val Ser Val
1               5                   10                  15

Lys Ser

<210> SEQ ID NO 9
<211> LENGTH: 18
<212> TYPE: PRT
<213> ORGANISM: Homo sapiens

<400> SEQUENCE: 9

Arg Ile Tyr Tyr Arg Ser Lys Trp Tyr Asn Ser Tyr Ala Val Ser Val
1               5                   10                  15

Lys Ser

<210> SEQ ID NO 10
<211> LENGTH: 18
<212> TYPE: PRT
<213> ORGANISM: Homo sapiens

<400> SEQUENCE: 10

Arg Ile Tyr Tyr Arg Ser Lys Trp Tyr Asn Ser Tyr Ala Val Ser Val
1               5                   10                  15

Lys Ser

<210> SEQ ID NO 11
<211> LENGTH: 18
<212> TYPE: PRT
<213> ORGANISM: Homo sapiens

<400> SEQUENCE: 11

Arg Ile Tyr Tyr Arg Ser Lys Trp Tyr Asn Asn Tyr Ala Val Ser Val
1               5                   10                  15

Lys Ser

<210> SEQ ID NO 12
<211> LENGTH: 18
<212> TYPE: PRT
<213> ORGANISM: Homo sapiens

<400> SEQUENCE: 12

Arg Ile Tyr Tyr Arg Ser Lys Trp Tyr Asn Ser Tyr Ala Val Ser Val
1               5                   10                  15

Lys Ser

<210> SEQ ID NO 13
<211> LENGTH: 18
<212> TYPE: PRT
```

<213> ORGANISM: Homo sapiens

<400> SEQUENCE: 13

Arg Ile Tyr Tyr Arg Ser Lys Trp Tyr Asn Ser Tyr Ala Val Ser Val
1               5                   10                  15

Lys Ser

<210> SEQ ID NO 14
<211> LENGTH: 18
<212> TYPE: PRT
<213> ORGANISM: Homo sapiens

<400> SEQUENCE: 14

Arg Ile Tyr Tyr Arg Ser Lys Trp Trp Asn Asp Tyr Ala Val Ser Val
1               5                   10                  15

Lys Ser

<210> SEQ ID NO 15
<211> LENGTH: 12
<212> TYPE: PRT
<213> ORGANISM: Homo sapiens

<400> SEQUENCE: 15

Tyr Asp Trp Val Pro Lys Ile Gly Val Phe Asp Ser
1               5                   10

<210> SEQ ID NO 16
<211> LENGTH: 12
<212> TYPE: PRT
<213> ORGANISM: Homo sapiens

<400> SEQUENCE: 16

Tyr Asp Trp Val Pro Lys Ile Gly Val Phe Asp Ser
1               5                   10

<210> SEQ ID NO 17
<211> LENGTH: 12
<212> TYPE: PRT
<213> ORGANISM: Homo sapiens

<400> SEQUENCE: 17

Tyr Asp Trp Val Pro Lys Ile Gly Val Phe Asp Ser
1               5                   10

<210> SEQ ID NO 18
<211> LENGTH: 12
<212> TYPE: PRT
<213> ORGANISM: Homo sapiens

<400> SEQUENCE: 18

Tyr Lys Trp Val Pro Lys Ile Gly Val Phe Asp Ser
1               5                   10

<210> SEQ ID NO 19
<211> LENGTH: 12
<212> TYPE: PRT
<213> ORGANISM: Homo sapiens

<400> SEQUENCE: 19

Tyr Gln Trp Val Pro Lys Ile Gly Val Phe Asp Ser
1               5                   10

<210> SEQ ID NO 20

```
<211> LENGTH: 12
<212> TYPE: PRT
<213> ORGANISM: Homo sapiens

<400> SEQUENCE: 20

Tyr Asp Trp Val Pro Lys Ile Gly Val Phe Asp Leu
1               5                   10

<210> SEQ ID NO 21
<211> LENGTH: 12
<212> TYPE: PRT
<213> ORGANISM: Homo sapiens

<400> SEQUENCE: 21

Tyr Asp Trp Val Pro Lys Ile Gly Val Phe Asp Gly
1               5                   10

<210> SEQ ID NO 22
<211> LENGTH: 12
<212> TYPE: PRT
<213> ORGANISM: Homo sapiens

<400> SEQUENCE: 22

Arg Ala Ser Gln Phe Ile Ser Ser Ser Tyr Leu Ser
1               5                   10

<210> SEQ ID NO 23
<211> LENGTH: 12
<212> TYPE: PRT
<213> ORGANISM: Homo sapiens

<400> SEQUENCE: 23

Arg Ala Ser Gln Met Ile Asp Leu Arg Tyr Leu Ser
1               5                   10

<210> SEQ ID NO 24
<211> LENGTH: 12
<212> TYPE: PRT
<213> ORGANISM: Homo sapiens

<400> SEQUENCE: 24

Arg Ala Ser Gln Phe Ile Ser Ser Ser Tyr Leu Ser
1               5                   10

<210> SEQ ID NO 25
<211> LENGTH: 12
<212> TYPE: PRT
<213> ORGANISM: Homo sapiens

<400> SEQUENCE: 25

Arg Ala Ser Gln Met Ile Asp Leu Arg Tyr Leu Ser
1               5                   10

<210> SEQ ID NO 26
<211> LENGTH: 12
<212> TYPE: PRT
<213> ORGANISM: Homo sapiens

<400> SEQUENCE: 26

Arg Ala Ser Gln Glu Ile Leu Pro Glu Tyr Leu Ser
1               5                   10

<210> SEQ ID NO 27
<211> LENGTH: 12
<212> TYPE: PRT
```

<213> ORGANISM: Homo sapiens

<400> SEQUENCE: 27

Arg Ala Ser Gln Trp Ile Glu Ala Gly Tyr Leu Ser
1               5                   10

<210> SEQ ID NO 28
<211> LENGTH: 12
<212> TYPE: PRT
<213> ORGANISM: Homo sapiens

<400> SEQUENCE: 28

Arg Ala Ser Gln Met Ile Asp Leu Arg Tyr Leu Ser
1               5                   10

<210> SEQ ID NO 29
<211> LENGTH: 11
<212> TYPE: PRT
<213> ORGANISM: Homo sapiens

<400> SEQUENCE: 29

Leu Leu Ile Tyr Gly Ser Ser Ser Arg Ala Thr
1               5                   10

<210> SEQ ID NO 30
<211> LENGTH: 11
<212> TYPE: PRT
<213> ORGANISM: Homo sapiens

<400> SEQUENCE: 30

Leu Leu Ile Tyr Gly Ser Ser Ser Arg Ala Thr
1               5                   10

<210> SEQ ID NO 31
<211> LENGTH: 11
<212> TYPE: PRT
<213> ORGANISM: Homo sapiens

<400> SEQUENCE: 31

Leu Leu Ile Tyr Gly Ser Ser Ser Arg Ala Thr
1               5                   10

<210> SEQ ID NO 32
<211> LENGTH: 11
<212> TYPE: PRT
<213> ORGANISM: Homo sapiens

<400> SEQUENCE: 32

Leu Leu Ile Tyr Gly Ser Ser Ser Arg Ala Thr
1               5                   10

<210> SEQ ID NO 33
<211> LENGTH: 11
<212> TYPE: PRT
<213> ORGANISM: Homo sapiens

<400> SEQUENCE: 33

Leu Leu Ile Tyr Gly Ser Ser Ser Arg Ala Thr
1               5                   10

<210> SEQ ID NO 34
<211> LENGTH: 11
<212> TYPE: PRT
<213> ORGANISM: Homo sapiens -continued

```
<400> SEQUENCE: 34

Leu Leu Ile Tyr Gly Ser Ser Ser Arg Ala Thr
1               5                   10

<210> SEQ ID NO 35
<211> LENGTH: 11
<212> TYPE: PRT
<213> ORGANISM: Homo sapiens

<400> SEQUENCE: 35

Leu Leu Ile Tyr Gly Ser Ser Ser Arg Ala Thr
1               5                   10

<210> SEQ ID NO 36
<211> LENGTH: 8
<212> TYPE: PRT
<213> ORGANISM: Homo sapiens

<400> SEQUENCE: 36

Gln Gln Val Tyr Asp Ile Pro Ile
1               5

<210> SEQ ID NO 37
<211> LENGTH: 8
<212> TYPE: PRT
<213> ORGANISM: Homo sapiens

<400> SEQUENCE: 37

Gln Gln Leu Tyr Ser Ser Pro Met
1               5

<210> SEQ ID NO 38
<211> LENGTH: 8
<212> TYPE: PRT
<213> ORGANISM: Homo sapiens

<400> SEQUENCE: 38

Gln Gln Leu Tyr Ser Ser Pro Met
1               5

<210> SEQ ID NO 39
<211> LENGTH: 8
<212> TYPE: PRT
<213> ORGANISM: Homo sapiens

<400> SEQUENCE: 39

Gln Gln Phe Tyr Ser Ser Pro Leu
1               5

<210> SEQ ID NO 40
<211> LENGTH: 8
<212> TYPE: PRT
<213> ORGANISM: Homo sapiens

<400> SEQUENCE: 40

Gln Gln Phe Tyr Ser Ser Pro Leu
1               5

<210> SEQ ID NO 41
<211> LENGTH: 8
<212> TYPE: PRT
<213> ORGANISM: Homo sapiens

<400> SEQUENCE: 41
```

```
Gln Gln Leu Tyr Ser Ser Pro Met
1               5
```

<210> SEQ ID NO 42
<211> LENGTH: 8
<212> TYPE: PRT
<213> ORGANISM: Homo sapiens

<400> SEQUENCE: 42

```
Gln Gln Phe Tyr Ser Ser Pro Leu
1               5
```

<210> SEQ ID NO 43
<211> LENGTH: 110
<212> TYPE: PRT
<213> ORGANISM: Homo sapiens

<400> SEQUENCE: 43

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Ile Ser Ser Ser
                20                  25                  30

Tyr Leu Ser Trp Tyr Gln Gln Lys Pro Gly Gln Ala Pro Arg Leu Leu
            35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Val Tyr Asp Ile Pro
                85                  90                  95

Ile Thr Phe Gly Gln Gly Thr Lys Val Glu Ile Lys Arg Thr
            100                 105                 110
```

<210> SEQ ID NO 44
<211> LENGTH: 110
<212> TYPE: PRT
<213> ORGANISM: Homo sapiens

<400> SEQUENCE: 44

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Met Ile Asp Leu Arg
                20                  25                  30

Tyr Leu Ser Trp Tyr Gln Gln Lys Pro Gly Gln Ala Pro Arg Leu Leu
            35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Leu Tyr Ser Ser Pro
                85                  90                  95

Met Thr Phe Gly Gln Gly Thr Lys Val Glu Ile Lys Arg Thr
            100                 105                 110
```

<210> SEQ ID NO 45
<211> LENGTH: 110
<212> TYPE: PRT
<213> ORGANISM: Homo sapiens

<400> SEQUENCE: 45

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Ile Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Leu Tyr Ser Ser Pro
                85                  90                  95

Met Thr Phe Gly Gln Gly Thr Lys Val Glu Ile Lys Arg Thr
            100                 105                 110

<210> SEQ ID NO 46
<211> LENGTH: 110
<212> TYPE: PRT
<213> ORGANISM: Homo sapiens

<400> SEQUENCE: 46

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Met Ile Asp Leu Arg
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Tyr Ser Ser Pro
                85                  90                  95

Leu Thr Phe Gly Gln Gly Thr Lys Val Glu Ile Lys Arg Thr
            100                 105                 110

<210> SEQ ID NO 47
<211> LENGTH: 110
<212> TYPE: PRT
<213> ORGANISM: Homo sapiens

<400> SEQUENCE: 47

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Glu Ile Leu Pro Glu
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Tyr Ser Ser Pro
                85                  90                  95

Leu Thr Phe Gly Gln Gly Thr Lys Val Glu Ile Lys Arg Thr
            100                 105                 110

<210> SEQ ID NO 48
<211> LENGTH: 110
<212> TYPE: PRT
<213> ORGANISM: Homo sapiens

<400> SEQUENCE: 48

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Trp Ile Glu Ala Gly
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Leu Tyr Ser Ser Pro
                85                  90                  95

Met Thr Phe Gly Gln Gly Thr Lys Val Glu Ile Lys Arg Thr
            100                 105                 110

<210> SEQ ID NO 49
<211> LENGTH: 110
<212> TYPE: PRT
<213> ORGANISM: Homo sapiens

<400> SEQUENCE: 49

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Met Ile Asp Leu Arg
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Tyr Ser Ser Pro
                85                  90                  95

Leu Thr Phe Gly Gln Gly Thr Lys Val Glu Ile Lys Arg Thr
            100                 105                 110

<210> SEQ ID NO 50
<211> LENGTH: 124
<212> TYPE: PRT
<213> ORGANISM: Homo sapiens

<400> SEQUENCE: 50

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser
            115                 120

<210> SEQ ID NO 51
<211> LENGTH: 124
<212> TYPE: PRT
<213> ORGANISM: Homo sapiens

<400> SEQUENCE: 51

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Gly Trp Ile Arg Gln Ser Pro Gly Arg Gly Leu Glu
            35                  40                  45

Trp Leu Gly Arg Ile Tyr Tyr Arg Ser Lys Trp Tyr Asn Ser Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser
            115                 120

<210> SEQ ID NO 52
<211> LENGTH: 124
<212> TYPE: PRT
<213> ORGANISM: Homo sapiens

<400> SEQUENCE: 52

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Gly Trp Ile Arg Gln Ser Pro Gly Arg Gly Leu Glu
            35                  40                  45

Trp Leu Gly Arg Ile Tyr Tyr Arg Ser Lys Trp Tyr Asn Ser Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser
            115                 120

<210> SEQ ID NO 53
<211> LENGTH: 124

<212> TYPE: PRT
<213> ORGANISM: Homo sapiens

<400> SEQUENCE: 53

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Asn Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Lys Trp Val Pro Lys Ile Gly Val Phe Asp
            100                 105                 110

Ser Trp Gly Gln Gly Thr Leu Val Thr Val Ser Ser
        115                 120

<210> SEQ ID NO 54
<211> LENGTH: 124
<212> TYPE: PRT
<213> ORGANISM: Homo sapiens

<400> SEQUENCE: 54

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Ser Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Gln Trp Val Pro Lys Ile Gly Val Phe Asp
            100                 105                 110

Ser Trp Gly Gln Gly Thr Leu Val Thr Val Ser Ser
        115                 120

<210> SEQ ID NO 55
<211> LENGTH: 124
<212> TYPE: PRT
<213> ORGANISM: Homo sapiens

<400> SEQUENCE: 55

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Ser Tyr Ala

```
            50                  55                  60
Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Tyr Asp Trp Val Pro Lys Ile Gly Val Phe Asp
                100                 105                 110

Leu Trp Gly Gln Gly Thr Leu Val Thr Val Ser Ser
            115                 120

<210> SEQ ID NO 56
<211> LENGTH: 124
<212> TYPE: PRT
<213> ORGANISM: Homo sapiens

<400> SEQUENCE: 56

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
                 20                  25                  30

Ser Ala Ala Trp Gly Trp Ile Arg Gln Ser Pro Gly Arg Gly Leu Glu
             35                  40                  45

Trp Leu Gly Arg Ile Tyr Tyr Arg Ser Lys Trp Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Tyr Asp Trp Val Pro Lys Ile Gly Val Phe Asp
                100                 105                 110

Gly Trp Gly Gln Gly Thr Leu Val Thr Val Ser Ser
            115                 120

<210> SEQ ID NO 57
<211> LENGTH: 330
<212> TYPE: DNA
<213> ORGANISM: Homo sapiens

<400> SEQUENCE: 57
gatatcgtgc tgacccagag cccggcgacc ctgagcctgt ctccgggcga acgtgcgacc     60
ctgagctgca gcgagcca gtttatttct tcttcttatc tgtcttggta ccagcagaaa    120
ccaggtcaag caccgcgtct attaatttat ggttcttctt ctcgtgcaac tggggtcccg    180
gcgcgtttta gcggctctgg atccggcacg gattttaccc tgaccattag cagcctggaa    240
cctgaagact ttgcggttta ttattgccag caggtttatg atattcctat tacctttggc    300
cagggtacga agttgaaat taaacgtacg                                     330

<210> SEQ ID NO 58
<211> LENGTH: 330
<212> TYPE: DNA
<213> ORGANISM: Homo sapiens

<400> SEQUENCE: 58
gatatcgtgc tgacccagag cccggcgacc ctgagcctgt ctccgggcga acgtgcgacc     60
ctgagctgca gcgagcca gatgattgat cttcgttatc tgtcttggta ccagcagaaa    120
ccaggtcaag caccgcgtct attaatttat ggttcttctt ctcgtgcaac tggggtcccg    180
```

```
gcgcgtttta gcggctctgg atccggcacg gattttaccc tgaccattag cagcctggaa    240
cctgaagact ttgcggtgta ttattgccag cagctttatt cttctcctat gacctttggc    300
cagggtacga aagttgaaat taaacgtacg                                     330
```

<210> SEQ ID NO 59
<211> LENGTH: 330
<212> TYPE: DNA
<213> ORGANISM: Homo sapiens

<400> SEQUENCE: 59

```
gatatcgtgc tgacccagag cccggcgacc ctgagcctgt ctccgggcga acgtgcgacc    60
ctgagctgca gagcgagcca gtttatttct tcttcttatc tgtcttggta ccagcagaaa    120
ccaggtcaag caccgcgtct attaatttat ggttcttctt ctcgtgcaac tggggtcccg    180
gcgcgtttta gcggctctgg atccggcacg gattttaccc tgaccattag cagcctggaa    240
cctgaagact ttgcggtgta ttattgccag cagctttatt cttctcctat gacctttggc    300
cagggtacga aagttgaaat taaacgtacg                                     330
```

<210> SEQ ID NO 60
<211> LENGTH: 330
<212> TYPE: DNA
<213> ORGANISM: Homo sapiens

<400> SEQUENCE: 60

```
gatatcgtgc tgacccagag cccggcgacc ctgagcctgt ctccgggcga acgtgcgacc    60
ctgagctgca gagcgagcca gatgattgat cttcgttatc tgtcttggta ccagcagaaa    120
ccaggtcaag caccgcgtct attaatttat ggttcttctt ctcgtgcaac tggggtcccg    180
gcgcgtttta gcggctctgg atccggcacg gattttaccc tgaccattag cagcctggaa    240
cctgaagact ttgcggtgta ttattgccag cagtttatt cttctcctct tacctttggc    300
cagggtacga aagttgaaat taaacgtacg                                     330
```

<210> SEQ ID NO 61
<211> LENGTH: 330
<212> TYPE: DNA
<213> ORGANISM: Homo sapiens

<400> SEQUENCE: 61

```
gatatcgtgc tgacccagag cccggcgacc ctgagcctgt ctccgggcga acgtgcgacc    60
ctgagctgca gagcgagcca ggagattctt cctgagtatc tgtcttggta ccagcagaaa    120
ccaggtcaag caccgcgtct attaatttat ggttcttctt ctcgtgcaac tggggtcccg    180
gcgcgtttta gcggctctgg atccggcacg gattttaccc tgaccattag cagcctggaa    240
cctgaagact ttgcggtgta ttattgccag cagtttatt cttctcctct tacctttggc    300
cagggtacga aagttgaaat taaacgtacg                                     330
```

<210> SEQ ID NO 62
<211> LENGTH: 330
<212> TYPE: DNA
<213> ORGANISM: Homo sapiens

<400> SEQUENCE: 62

```
gatatcgtgc tgacccagag cccggcgacc ctgagcctgt ctccgggcga acgtgcgacc    60
ctgagctgca gagcgagcca gtggattgag gctggttatc tgtcttggta ccagcagaaa    120
```

```
ccaggtcaag caccgcgtct attaatttat ggttcttctt ctcgtgcaac tggggtcccg      180
gcgcgtttta gcggctctgg atccggcacg gattttaccc tgaccattag cagcctggaa      240
cctgaagact ttgcggtgta ttattgccag cagctttatt cttctcctat gacctttggc      300
cagggtacga aagttgaaat taaacgtacg                                        330

<210> SEQ ID NO 63
<211> LENGTH: 330
<212> TYPE: DNA
<213> ORGANISM: Homo sapiens

<400> SEQUENCE: 63
gatatcgtgc tgacccagag cccggcgacc ctgagcctgt ctccgggcga acgtgcgacc      60
ctgagctgca gcgcgagcca gatgattgat cttcgttatc tgtcttggta ccagcagaaa     120
ccaggtcaag caccgcgtct attaatttat ggttcttctt ctcgtgcaac tggggtcccg     180
gcgcgtttta gcggctctgg atccggcacg gattttaccc tgaccattag cagcctggaa     240
cctgaagact ttgcggtgta ttattgccag cagtttatt cttctcctct tacctttggc     300
cagggtacga aagttgaaat taaacgtacg                                        330

<210> SEQ ID NO 64
<211> LENGTH: 372
<212> TYPE: DNA
<213> ORGANISM: Homo sapiens

<400> SEQUENCE: 64
caggtgcaat tgcaacagtc tggtccgggc ctggtgaaac cgagccaaac cctgagcctg      60
acctgtgcga tttccggaga tagcgtgagc tctaattctg ctgcttgggg ttggattcgc     120
cagtctcctg ggcgtggcct cgagtggctg ggccgtatct attatcgtag caagtggtat     180
aacgattatg cggtgagcgt gaaaagccgg attaccatca cccggatac ttcgaaaaac      240 cagtttagcc tgcaactgaa cagcgtgacc ccggaagata cggccgtgta ttattgcgcg     300
cgttatgatt gggttcctaa gattggtgtt tttgattctt ggggccaagg caccctggtg     360
acggttagct ca                                                          372

<210> SEQ ID NO 65
<211> LENGTH: 372
<212> TYPE: DNA
<213> ORGANISM: Homo sapiens

<400> SEQUENCE: 65
caggtgcaat tgcaacagtc tggtccgggc ctggtgaaac cgagccaaac cctgagcctg      60
acctgtgcga tttccggaga tagcgtgagc tctaattctg ctgcttgggg ttggattcgc     120
cagtctcctg ggcgtggcct cgagtggctg ggccgtatct attatcgtag caagtggtat     180
aactcttatg cggtgagcgt gaaaagccgg attaccatca cccggatac ttcgaaaaac      240 cagtttagcc tgcaactgaa cagcgtgacc ccggaagata cggccgtgta ttattgcgcg     300
cgttatgatt gggttcctaa gattggtgtt tttgattctt ggggccaagg caccctggtg     360
acggttagct ca                                                          372

<210> SEQ ID NO 66
<211> LENGTH: 372
<212> TYPE: DNA
<213> ORGANISM: Homo sapiens

<400> SEQUENCE: 66
```

```
caggtgcaat tgcaacagtc tggtccgggc ctggtgaaac cgagccaaac cctgagcctg    60
acctgtgcga tttccggaga tagcgtgagc tctaattctg ctgcttgggg ttggattcgc   120
cagtctcctg ggcgtggcct cgagtggctg ggccgtatct attatcgtag caagtggtat   180
aactcttatg cggtgagcgt gaaaagccgg attaccatca acccggatac ttcgaaaaac   240
cagtttagcc tgcaactgaa cagcgtgacc ccggaagata cggccgtgta ttattgcgcg   300
cgttatgatt gggttcctaa gattggtgtt tttgattctt ggggccaagg caccctggtg   360
acggttagct ca                                                       372
```

<210> SEQ ID NO 67
<211> LENGTH: 372
<212> TYPE: DNA
<213> ORGANISM: Homo sapiens

<400> SEQUENCE: 67

```
caggtgcaat tgcaacagtc tggtccgggc ctggtgaaac cgagccaaac cctgagcctg    60
acctgtgcga tttccggaga tagcgtgagc tctaattctg ctgcttgggg ttggattcgc   120
cagtctcctg ggcgtggcct cgagtggctg ggccgtatct attatcgtag caagtggtat   180
aacaattatg cggtgagcgt gaaaagccgg attaccatca acccggatac ttcgaaaaac   240
cagtttagcc tgcaactgaa cagcgtgacc ccggaagata cggccgtgta ttattgcgcg   300
cgttataagt gggttcctaa gattggtgtt tttgattctt ggggccaagg caccctggtg   360
acggttagct ca                                                       372
```

<210> SEQ ID NO 68
<211> LENGTH: 372
<212> TYPE: DNA
<213> ORGANISM: Homo sapiens

<400> SEQUENCE: 68

```
caggtgcaat tgcaacagtc tggtccgggc ctggtgaaac cgagccaaac cctgagcctg    60
acctgtgcga tttccggaga tagcgtgagc tctaattctg ctgcttgggg ttggattcgc   120
cagtctcctg ggcgtggcct cgagtggctg ggccgtatct attatcgtag caagtggtat   180
aactcttatg cggtgagcgt gaaaagccgg attaccatca acccggatac ttcgaaaaac   240
cagtttagcc tgcaactgaa cagcgtgacc ccggaagata cggccgtgta ttattgcgcg   300
cgttatcagt gggttcctaa gattggtgtt tttgattctt ggggccaagg caccctggtg   360
acggttagct ca                                                       372
```

<210> SEQ ID NO 69
<211> LENGTH: 372
<212> TYPE: DNA
<213> ORGANISM: Homo sapiens

<400> SEQUENCE: 69

```
caggtgcaat tgcaacagtc tggtccgggc ctggtgaaac cgagccaaac cctgagcctg    60
acctgtgcga tttccggaga tagcgtgagc tctaattctg ctgcttgggg ttggattcgc   120
cagtctcctg ggcgtggcct cgagtggctg ggccgtatct attatcgtag caagtggtat   180
aactcttatg cggtgagcgt gaaaagccgg attaccatca acccggatac ttcgaaaaac   240
cagtttagcc tgcaactgaa cagcgtgacc ccggaagata cggccgtgta ttattgcgcg   300
cgttatgatt gggttcctaa gattggtgtt tttgatcttt ggggccaagg caccctggtg   360
```

-continued acggttagct ca                                                    372

<210> SEQ ID NO 70
<211> LENGTH: 372
<212> TYPE: DNA
<213> ORGANISM: Homo sapiens

<400> SEQUENCE: 70
caggtgcaat tgcaacagtc tggtccgggc ctggtgaaac cgagccaaac cctgagcctg     60
acctgtgcga tttccggaga tagcgtgagc tctaattctg ctgcttgggg ttggattcgc    120
cagtctcctg gcgtggcct cgagtggctg gccgtatct attatcgtag caagtggtgg      180
aacgattatg cggtgagcgt gaaaagccgg attaccatca acccggatac ttcgaaaaac    240
cagtttagcc tgcaactgaa cagcgtgacc ccggaagata cggccgtgta ttattgcgcg    300
cgttatgatt gggttcctaa gattggtgtt tttgatgggt ggggccaagg caccctggtg    360
acggttagct ca                                                        372

<210> SEQ ID NO 71
<211> LENGTH: 215
<212> TYPE: PRT
<213> ORGANISM: Homo sapiens

<400> SEQUENCE: 71

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Ile Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Leu Tyr Ser Ser Pro
                85                  90                  95

Met Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 72
<211> LENGTH: 215
<212> TYPE: PRT
<213> ORGANISM: Homo sapiens

```
<400> SEQUENCE: 72

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Met Ile Asp Leu Arg
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Tyr Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 73
<211> LENGTH: 215
<212> TYPE: PRT
<213> ORGANISM: Homo sapiens

<400> SEQUENCE: 73

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Glu Ile Leu Pro Glu
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Tyr Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140
```

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 74
<211> LENGTH: 215
<212> TYPE: PRT
<213> ORGANISM: Homo sapiens

<400> SEQUENCE: 74

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Met Ile Asp Leu Arg
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Tyr Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 75
<211> LENGTH: 454
<212> TYPE: PRT
<213> ORGANISM: Homo sapiens

<400> SEQUENCE: 75

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

```
Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Ser Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445
```

```
Ser Leu Ser Pro Gly Lys
            450

<210> SEQ ID NO 76
<211> LENGTH: 454
<212> TYPE: PRT
<213> ORGANISM: Homo sapiens

<400> SEQUENCE: 76

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Asn Tyr Ala
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Tyr Lys Trp Val Pro Lys Ile Gly Val Phe Asp
        100                 105                 110

Ser Trp Gly Gln Gly Thr Leu Val Thr Val Ser Ser Ala Ser Thr Lys
    115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365
```

```
Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
        450

<210> SEQ ID NO 77
<211> LENGTH: 454
<212> TYPE: PRT
<213> ORGANISM: Homo sapiens

<400> SEQUENCE: 77

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Ser Tyr Ala
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Gln Trp Val Pro Lys Ile Gly Val Phe Asp
            100                 105                 110

Ser Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
```

```
            275                 280                 285
Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 78
<211> LENGTH: 454
<212> TYPE: PRT
<213> ORGANISM: Homo sapiens

<400> SEQUENCE: 78

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Trp Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Gly Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

Val Thr Val Pro Ser Ser Leu Gly Thr Gln Thr Tyr Ile Cys Asn
            195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
    435                 440                 445

Ser Leu Ser Pro Gly Lys
    450

<210> SEQ ID NO 79
<211> LENGTH: 1362
<212> TYPE: DNA
<213> ORGANISM: Homo sapiens

<400> SEQUENCE: 79
caggtgcagc tgcagcagag cggcccaggc ctggtcaagc cctctcagac cctgtcactg      60
acctgcgcca tttcaggcga cagcgtgagc agcaacagcg ccgcctgggg ctggatcagg     120
cagagccccg tagggggcct ggaatggctg ggcaggatct actacaggtc caagtggtac     180
aacagctacg ccgtgagcgt gaagagcagg atcaccatca accctgacac cagcaagaac     240
cagttctcac tgcagctcaa cagcgtgacc cccgaggaca ccgccgtgta ctactgcgcc     300
agatacgact gggtgcccaa gatcggcgtg ttcgacagct ggggccaggg caccctggtg     360
accgtgtcaa gcgccagcac caagggcccc agcgtgttcc ccctggcccc cagcagcaag     420
agcaccagcg gcggcacagc cgccctgggc tgcctggtga aggactactt ccccgagccc     480
gtgaccgtgt cctggaacag cggagccctg acctccggcg tgcacacctt ccccgccgtg     540
ctgcagagca gcggcctgta cagcctgtcc agcgtggtga cagtgcccag cagcagcctg     600

```
ggcacccaga cctacatctg caacgtgaac cacaagccca gcaacaccaa ggtggacaag    660
agagtggagc ccaagagctg cgacaagacc cacacctgcc cccctgccc agccccagag    720 ctgctgggcg gaccctccgt gttcctgttc ccccccaagc ccaaggacac cctgatgatc    780
agcaggaccc ccgaggtgac ctgcgtggtg gtggacgtga gccacgagga cccagaggtg    840
aagttcaact ggtacgtgga cggcgtggag gtgcacaacg ccaagaccaa gcccagagag    900
gagcagtaca acagcaccta cagggtggtg tccgtgctga ccgtgctgca ccaggactgg    960
ctgaacggca aggaatacaa gtgcaaggtc tccaacaagg ccctgccagc ccccatcgaa   1020
aagaccatca gcaaggccaa gggccagcca cgggagcccc aggtgtacac cctgccccc    1080 tcccgggagg agatgaccaa gaaccaggtg tccctgacct gtctggtgaa gggcttctac   1140
cccagcgaca tcgccgtgga gtgggagagc aacggccagc ccgagaacaa ctacaagacc   1200 accccccag tgctggacag cgacggcagc ttcttcctgt acagcaagct gaccgtggac   1260
aagtccaggt ggcagcaggg caacgtgttc agctgcagcg tgatgcacga ggccctgcac   1320
aaccactaca cccagaagag cctgagcctg tccccccggca ag                     1362
```

<210> SEQ ID NO 80
<211> LENGTH: 1362
<212> TYPE: DNA
<213> ORGANISM: Homo sapiens

<400> SEQUENCE: 80

```
caggtgcagc tgcagcagag cggcccaggc ctggtgaagc cctctcagac cctgagcctg     60
acctgcgcca tcagcggcga cagcgtgagc agcaacagcg ccgcctgggg ctggatcagg    120
cagagccccg cagggggcct ggaatggctg ggcaggatct actataggtc caagtggtac    180
aacaactacg ccgtgagcgt gaagagcagg atcaccatca ccccgacac cagcaagaac    240 cagttcagcc tgcagctcaa cagcgtgacc cccgaggaca ccgccgtgta ctactgcgcc    300
aggtacaagt gggtgcccaa gatcggcgtg ttcgacagct ggggccaggg caccctggtg    360
accgtgagca gcgctagcac caagggcccc agcgtgttcc cctggcccc agcagcaag    420 agcaccagcg gcggcacagc cgccctgggc tgcctggtga aggactactt ccccgagccc    480
gtgaccgtgt cctggaacag cggagccctg acctccggcg tgcacacctt ccccgccgtg    540
ctgcagagca gcggcctgta cagcctgtcc agcgtggtga cagtgcccag cagcagcctg    600
ggcacccaga cctacatctg caacgtgaac cacaagccca gcaacaccaa ggtggacaag    660
agagtggagc ccaagagctg cgacaagacc cacacctgcc cccctgccc agccccagag    720 ctgctgggcg gaccctccgt gttcctgttc ccccccaagc ccaaggacac cctgatgatc    780
agcaggaccc ccgaggtgac ctgcgtggtg gtggacgtga gccacgagga cccagaggtg    840
aagttcaact ggtacgtgga cggcgtggag gtgcacaacg ccaagaccaa gcccagagag    900
gagcagtaca acagcaccta cagggtggtg tccgtgctga ccgtgctgca ccaggactgg    960
ctgaacggca aggaatacaa gtgcaaggtc tccaacaagg ccctgccagc ccccatcgaa   1020
aagaccatca gcaaggccaa gggccagcca cgggagcccc aggtgtacac cctgccccc    1080 tcccgggagg agatgaccaa gaaccaggtg tccctgacct gtctggtgaa gggcttctac   1140
cccagcgaca tcgccgtgga gtgggagagc aacggccagc ccgagaacaa ctacaagacc   1200 accccccag tgctggacag cgacggcagc ttcttcctgt acagcaagct gaccgtggac   1260
aagtccaggt ggcagcaggg caacgtgttc agctgcagcg tgatgcacga ggccctgcac   1320
aaccactaca cccagaagag cctgagcctg tccccccggca ag                     1362
```

<210> SEQ ID NO 81
<211> LENGTH: 1362
<212> TYPE: DNA
<213> ORGANISM: Homo sapiens

<400> SEQUENCE: 81

```
caggtgcagc tgcagcagag cggcccaggc ctggtgaagc cctctcagac cctgagcctg      60
acctgcgcca tcagcggcga cagcgtgagc agcaacagcg ccgcctgggg ctggatcagg     120
cagagccccg caggggcct ggaatggctg ggcaggatct actataggtc caagtggtac     180
aacagctacg ccgtgagcgt gaagagcagg atcaccatca accccgacac cagcaagaac     240
cagttcagcc tgcagctcaa cagcgtgacc cccgaggaca ccgccgtgta ctactgcgcc     300
aggtatcagt gggtgcccaa gatcggcgtg ttcgacagct ggggccaggg caccctggtg     360
accgtgagca gcgctagcac caagggcccc agcgtgttcc ccctggcccc cagcagcaag     420
agcaccagcg gcggcacagc cgccctgggc tgcctggtga aggactactt ccccgagccc     480
gtgaccgtgt cctggaacag cggagccctg acctccggcg tgcacacctt ccccgccgtg     540
ctgcagagca gcggcctgta cagcctgtcc agcgtggtga cagtgcccag cagcagcctg     600
ggcacccaga cctacatctg caacgtgaac cacaagccca gcaacaccaa ggtggacaag     660
agagtggagc ccaagagctg cgacaagacc cacacctgcc cccctgccc agccccagag     720
ctgctgggcg gacccctccgt gttcctgttc ccccccaagc ccaaggacac cctgatgatc     780
agcaggaccc ccgaggtgac ctgcgtggtg gtggacgtga gccacgagga cccagaggtg     840
aagttcaact ggtacgtgga cggcgtggag gtgcacaacg ccaagaccaa gcccagagag     900
gagcagtaca acagcaccta cagggtggtg tccgtgctga ccgtgctgca ccaggactgg     960
ctgaacggca aggaatacaa gtgcaaggtc tccaacaagg ccctgccagc ccccatcgaa    1020
aagaccatca gcaaggccaa gggccagcca cgggagcccc aggtgtacac cctgccccc     1080
tcccgggagg agatgaccaa gaaccaggtg tccctgacct gtctggtgaa gggcttctac    1140
cccagcgaca tcgccgtgga gtgggagagc aacggccagc ccgagaacaa ctacaagacc    1200
accccccag tgctggacag cgacggcagc ttcttcctgt acagcaagct gaccgtggac    1260
aagtccaggt ggcagcaggg caacgtgttc agctgcagcg tgatgcacga ggccctgcac    1320
aaccactaca cccagaagag cctgagcctg tcccccggca ag                      1362
```

<210> SEQ ID NO 82
<211> LENGTH: 1362
<212> TYPE: DNA
<213> ORGANISM: Homo sapiens

<400> SEQUENCE: 82

```
caggtgcagc tgcagcagag cggcccaggc ctggtgaagc cctctcagac cctgagcctg      60
acctgcgcca tcagcggcga cagcgtgagc agcaacagcg ccgcctgggg ctggatcagg     120
cagagccccg caggggcct ggaatggctg ggcaggatct actataggtc caagtggtgg     180
aacgactacg ccgtgagcgt gaagagcagg atcaccatca accccgacac cagcaagaac     240
cagttcagcc tgcagctcaa cagcgtgacc cccgaggaca ccgccgtgta ctactgcgcc     300
agatatgact gggtgcccaa gatcggcgtg ttcgacggct ggggccaggg caccctggtg     360
accgtgagca gcgctagcac caagggcccc agcgtgttcc ccctggcccc cagcagcaag     420
agcaccagcg gcggcacagc cgccctgggc tgcctggtga aggactactt ccccgagccc     480
```

```
gtgaccgtgt cctggaacag cggagccctg acctccggcg tgcacacctt ccccgccgtg      540
ctgcagagca gcggcctgta cagcctgtcc agcgtggtga cagtgcccag cagcagcctg      600
ggcacccaga cctacatctg caacgtgaac cacaagccca gcaacaccaa ggtggacaag      660
agagtggagc ccaagagctg cgacaagacc cacacctgcc cccctgccc agccccagag       720 ctgctgggcg gaccctccgt gttcctgttc ccccccaagc caaggacac cctgatgatc       780 agcaggaccc ccgaggtgac ctgcgtggtg gtggacgtga gccacgagga cccagaggtg      840
aagttcaact ggtacgtgga cggcgtggag gtgcacaacg ccaagaccaa gcccagagag      900
gagcagtaca acagcaccta cagggtggtg tccgtgctga ccgtgctgca ccaggactgg      960
ctgaacggca aggaatacaa gtgcaaggtc tccaacaagg ccctgccagc ccccatcgaa     1020
aagaccatca gcaaggccaa gggccagcca cgggagcccc aggtgtacac cctgcccccc     1080
tcccgggagg agatgaccaa gaaccaggtg tccctgacct gtctggtgaa gggcttctac     1140
cccagcgaca tcgccgtgga gtgggagagc aacggccagc ccgagaacaa ctacaagacc     1200
acccccccag tgctggacag cgacggcagc ttcttcctgt acagcaagct gaccgtggac     1260
aagtccaggt ggcagcaggg caacgtgttc agctgcagcg tgatgcacga ggccctgcac     1320
aaccactaca cccagaagag cctgagcctg tcccccggca ag                       1362

<210> SEQ ID NO 83
<211> LENGTH: 645
<212> TYPE: DNA
<213> ORGANISM: Homo sapiens

<400> SEQUENCE: 83
gatatcgtgc tgacacagag ccccgccacc ctgagcctga gcccaggcga gagggccacc       60
ctgtcctgca gggccagcca gtttatcagc agcagctacc tgtcctggta tcagcagaag      120
cccggccagg cccctagact gctgatctac ggcagctcct ctcgggccac cggcgtgccc      180
gccaggttca gcggcagcgg ctccggcacc gacttcaccc tgacaatcag cagcctggag      240
cccgaggact tcgccgtgta ctactgccag cagctgtaca gctcacccat gaccttcggc      300
cagggcacca aggtggagat caagcgtacg gtggccgctc ccagcgtgtt catcttcccc      360
cccagcgacg agcagctgaa gagcggcacc gccagcgtgg tgtgcctgct gaacaacttc      420
taccccgggg aggccaaggt gcagtggaag gtggacaacg ccctgcagag cggcaacagc      480
caggagagcg tcaccgagca ggacagcaag gactccacct acagcctgag cagcaccctg      540
accctgagca aggccgacta cgagaagcat aaggtgtacg cctgcgaggt gacccaccag      600
ggcctgtcca gcccgtgac caagagcttc aacaggggcg agtgc                      645

<210> SEQ ID NO 84
<211> LENGTH: 645
<212> TYPE: DNA
<213> ORGANISM: Homo sapiens

<400> SEQUENCE: 84
gacatcgtgc tgacacagag ccccgccacc ctgagcctga gcccaggcga gagggccacc       60
ctgtcctgta gggccagcca gatgatcgac ctgagatacc tgagctggta tcagcagaag      120
cccggccagg cccccaggct cctgatctac ggcagctcta gcagggctac cggcgtgccc      180
gccaggttca gcggcagcgg ctccggcacc gacttcaccc tgaccatctc aagcctggaa      240
cccgaggact tcgccgtgta ctactgccag cagttctaca gcagccccct gaccttcggc      300
cagggcacca aggtggagat caagcgtacg gtggccgctc ccagcgtgtt catcttcccc      360
```

```
cccagcgacg agcagctgaa gagcggcacc gccagcgtgg tgtgcctgct gaacaacttc      420
taccccsggg aggccaaggt gcagtggaag gtggacaacg ccctgcagag cggcaacagc      480
caggagagcg tcaccgagca ggacagcaag gactccacct acagcctgag cagcaccctg      540
accctgagca aggccgacta cgagaagcat aaggtgtacg cctgcgaggt gacccaccag      600
ggcctgtcca gccccgtgac caagagcttc aacaggggcg agtgc                     645
```

<210> SEQ ID NO 85
<211> LENGTH: 645
<212> TYPE: DNA
<213> ORGANISM: Homo sapiens

<400> SEQUENCE: 85

```
gacatcgtgc tgacacagag ccccgccacc ctgagcctga gcccaggcga gagggccacc       60
ctgtcctgta gggccagcca ggaaatcctg cccgagtacc tgagctggta tcagcagaag      120
cccggccagg cccccaggct cctgatctac ggcagctcta gcagggctac cggcgtgccc      180
gccaggttca gcggcagcgg ctccggcacc gacttcaccc tgaccatctc aagcctggaa      240
cccgaggact cgccgtgta ctactgccag cagttctaca gcagccccct gaccttcggc       300
cagggcacca aggtggagat caagcgtacg gtggccgctc ccagcgtgtt catcttcccc      360
cccagcgacg agcagctgaa gagcggcacc gccagcgtgg tgtgcctgct gaacaacttc      420
taccccsggg aggccaaggt gcagtggaag gtggacaacg ccctgcagag cggcaacagc      480
caggagagcg tcaccgagca ggacagcaag gactccacct acagcctgag cagcaccctg      540
accctgagca aggccgacta cgagaagcat aaggtgtacg cctgcgaggt gacccaccag      600
ggcctgtcca gccccgtgac caagagcttc aacaggggcg agtgc                     645
```

<210> SEQ ID NO 86
<211> LENGTH: 645
<212> TYPE: DNA
<213> ORGANISM: Homo sapiens

<400> SEQUENCE: 86

```
gacatcgtgc tgacacagag ccccgccacc ctgagcctga gcccaggcga gagggccacc       60
ctgtcctgta gggccagcca gatgatcgac ctgagatacc tgagctggta tcagcagaag      120
cccggccagg cccccaggct cctgatctac ggcagctcta gcagggctac cggcgtgccc      180
gccaggttca gcggcagcgg ctccggcacc gacttcaccc tgaccatctc aagcctggaa      240
cccgaggact cgccgtgta ctactgccag cagttctaca gcagccccct gaccttcggc       300
cagggcacca aggtggagat caagcgtacg gtggccgctc ccagcgtgtt catcttcccc      360
cccagcgacg agcagctgaa gagcggcacc gccagcgtgg tgtgcctgct gaacaacttc      420
taccccsggg aggccaaggt gcagtggaag gtggacaacg ccctgcagag cggcaacagc      480
caggagagcg tcaccgagca ggacagcaag gactccacct acagcctgag cagcaccctg      540
accctgagca aggccgacta cgagaagcat aaggtgtacg cctgcgaggt gacccaccag      600
ggcctgtcca gccccgtgac caagagcttc aacaggggcg agtgc                     645
```

<210> SEQ ID NO 87
<211> LENGTH: 184
<212> TYPE: PRT
<213> ORGANISM: Homo sapiens

<400> SEQUENCE: 87

```
Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
            35                  40                  45

Ser Ser Pro Ala Pro Arg Thr Ala Leu Gln Pro Gln Glu Ser Val Gly
    50                  55                  60

Ala Gly Ala Gly Glu Ala Ala Leu Pro Leu Pro Gly Leu Leu Phe Gly
65                  70                  75                  80

Ala Pro Ala Leu Leu Gly Leu Ala Leu Val Leu Ala Leu Val Leu Val
                85                  90                  95

Gly Leu Val Ser Trp Arg Arg Arg Gln Arg Arg Leu Arg Gly Ala Ser
                100                 105                 110

Ser Ala Glu Ala Pro Asp Gly Asp Lys Asp Ala Pro Glu Pro Leu Asp
            115                 120                 125

Lys Val Ile Ile Leu Ser Pro Gly Ile Ser Asp Ala Thr Ala Pro Ala
    130                 135                 140

Trp Pro Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
            180

<210> SEQ ID NO 88
<211> LENGTH: 24
<212> TYPE: PRT
<213> ORGANISM: Homo sapiens

<400> SEQUENCE: 88

Pro Thr Pro Cys Val Pro Ala Glu Cys Phe Asp Leu Leu Val Arg His
1               5                   10                  15

Cys Val Ala Cys Gly Leu Leu Arg
                20
```